(12) United States Patent
Schlesinger et al.

(10) Patent No.: US 10,376,134 B2
(45) Date of Patent: Aug. 13, 2019

(54) SYSTEMS AND METHODS FOR REDUCING MEASUREMENT ERROR USING OPTICAL FIBER SHAPE SENSORS

(71) Applicant: Intuitive Surgical Operations, Inc., Sunnyvale, CA (US)

(72) Inventors: Randall L. Schlesinger, San Mateo, CA (US); Stephen J. Blumenkranz, Los Altos Hills, CA (US); Christopher R. Carlson, Belmont, CA (US); Vincent Duindam, San Francisco, CA (US); Anoop B. Kowshik, Saratoga, CA (US); Timothy D. Soper, San Jose, CA (US)

(73) Assignee: Intutitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/518,385

(22) PCT Filed: Oct. 16, 2015

(86) PCT No.: PCT/US2015/055879
§ 371 (c)(1),
(2) Date: Apr. 11, 2017

(87) PCT Pub. No.: WO2016/061431
PCT Pub. Date: Apr. 21, 2016

(65) Prior Publication Data
US 2017/0303824 A1   Oct. 26, 2017

Related U.S. Application Data

(60) Provisional application No. 62/065,349, filed on Oct. 17, 2014.

(51) Int. Cl.
*A61B 1/00* (2006.01)
*G02B 6/12* (2006.01)
(Continued)

(52) U.S. Cl.
CPC ........ *A61B 1/00096* (2013.01); *A61B 1/0051* (2013.01); *A61B 1/0055* (2013.01);
(Continued)

(58) Field of Classification Search
CPC ............. A61B 1/00096; A61B 1/0051; A61B 1/00078; A61B 2034/2061
(Continued)

(56) References Cited

U.S. PATENT DOCUMENTS 5,514,236 A   5/1996 Avellanet et al.
6,380,732 B1   4/2002 Gilboa
(Continued)

FOREIGN PATENT DOCUMENTS

EP   3000379 A1   3/2016
JP   H0373123 A   3/1991
(Continued)

OTHER PUBLICATIONS

International Search Report and Written Opinion for Application No. PCT/US2015/055879, dated Jan. 26, 2016, 12 pages.
(Continued)

*Primary Examiner* — Robert Tavlykaev
(74) *Attorney, Agent, or Firm* — Haynes and Boone, LLP

(57) ABSTRACT

An apparatus comprises an instrument including an elongated shaft. The apparatus also comprises a first shape sensor including an elongated optical fiber extending within the elongated shaft at a first radial distance from the neutral axis. The apparatus also comprises a twist resistant feature configured to reduce twisting of the elongated optical fiber relative to the elongated shaft while permitting axial translation of the elongated optical fiber within the elongated shaft.

23 Claims, 15 Drawing Sheets

(51) Int. Cl.
  *A61B 1/005* (2006.01)
  *A61B 1/018* (2006.01)
  *A61B 34/20* (2016.01)

(52) U.S. Cl.
  CPC .......... *A61B 1/00078* (2013.01); *A61B 1/018* (2013.01); *A61B 2034/2061* (2016.02)

(58) Field of Classification Search
  USPC .... 385/12, 13, 117, 118; 600/104, 106, 145, 600/342, 478, 182, 202; 606/15, 16
  See application file for complete search history.

(56) References Cited

U.S. PATENT DOCUMENTS

| | | | |
|---|---|---|---|
| 6,389,187 B1 | 5/2002 | Greenaway et al. | |
| 7,772,541 B2 | 8/2010 | Froggatt et al. | |
| 7,781,724 B2 | 8/2010 | Childers et al. | |
| 8,900,131 B2 | 12/2014 | Chopra et al. | |
| 9,066,739 B2 | 6/2015 | Larkin et al. | |
| 2003/0130564 A1 | 7/2003 | Martone et al. | |
| 2005/0273090 A1* | 12/2005 | Nieman | A61B 18/14 606/15 |
| 2006/0013523 A1 | 1/2006 | Childers et al. | |
| 2006/0079735 A1 | 4/2006 | Martone et al. | |
| 2007/0156019 A1 | 7/2007 | Larkin et al. | |
| 2011/0202069 A1* | 8/2011 | Prisco | G01D 5/35316 606/130 |
| 2013/0028554 A1* | 1/2013 | Wong | A61B 5/065 385/12 |
| 2013/0090552 A1 | 4/2013 | Ramamurthy et al. | |
| 2013/0096572 A1 | 4/2013 | Donhowe et al. | |
| 2013/0345719 A1 | 12/2013 | Donhowe et al. | |
| 2014/0275997 A1 | 9/2014 | Chopra et al. | |
| 2016/0073863 A1* | 3/2016 | Kuboi | G02B 23/2476 600/117 |
| 2016/0081761 A1* | 3/2016 | Kuboi | A61B 1/00004 600/424 |
| 2016/0228199 A1* | 8/2016 | Flexman | G02B 23/2476 |
| 2016/0327781 A1* | 11/2016 | Kuboi | A61B 1/07 |
| 2017/0020612 A1* | 1/2017 | Kuboi | G02B 23/26 |

FOREIGN PATENT DOCUMENTS

| | | |
|---|---|---|
| JP | H11285468 A | 10/1999 |
| JP | 2014142228 A | 8/2014 |
| WO | WO-2011100124 A1 | 8/2011 |
| WO | WO-2014049519 A1 | 4/2014 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2015/055879, dated Apr. 27, 2017, 9 pages.

Extended European Search Report for Application No. EP15849881. 6, dated Jun. 20, 2018, 7 pages.

* cited by examiner

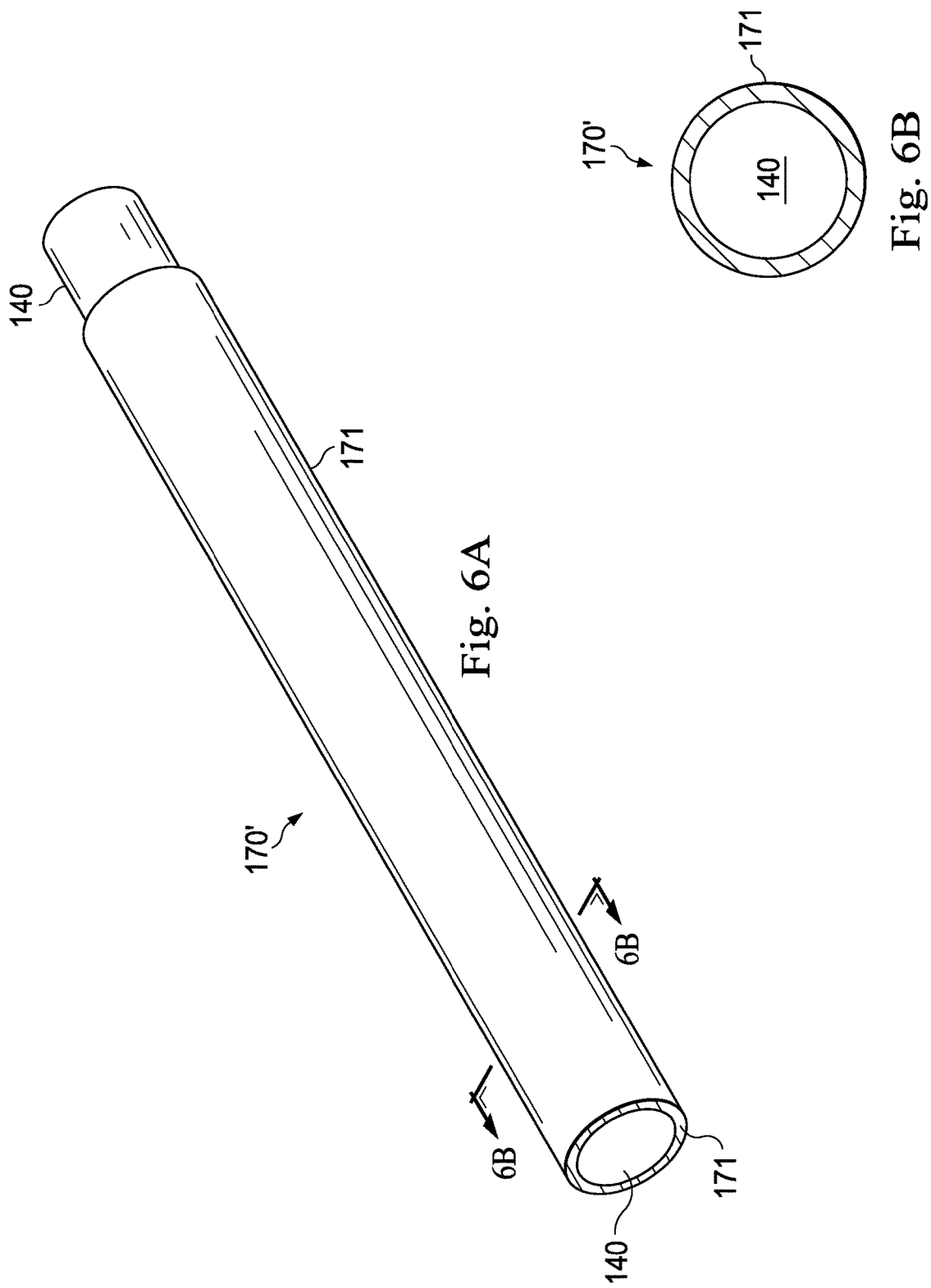

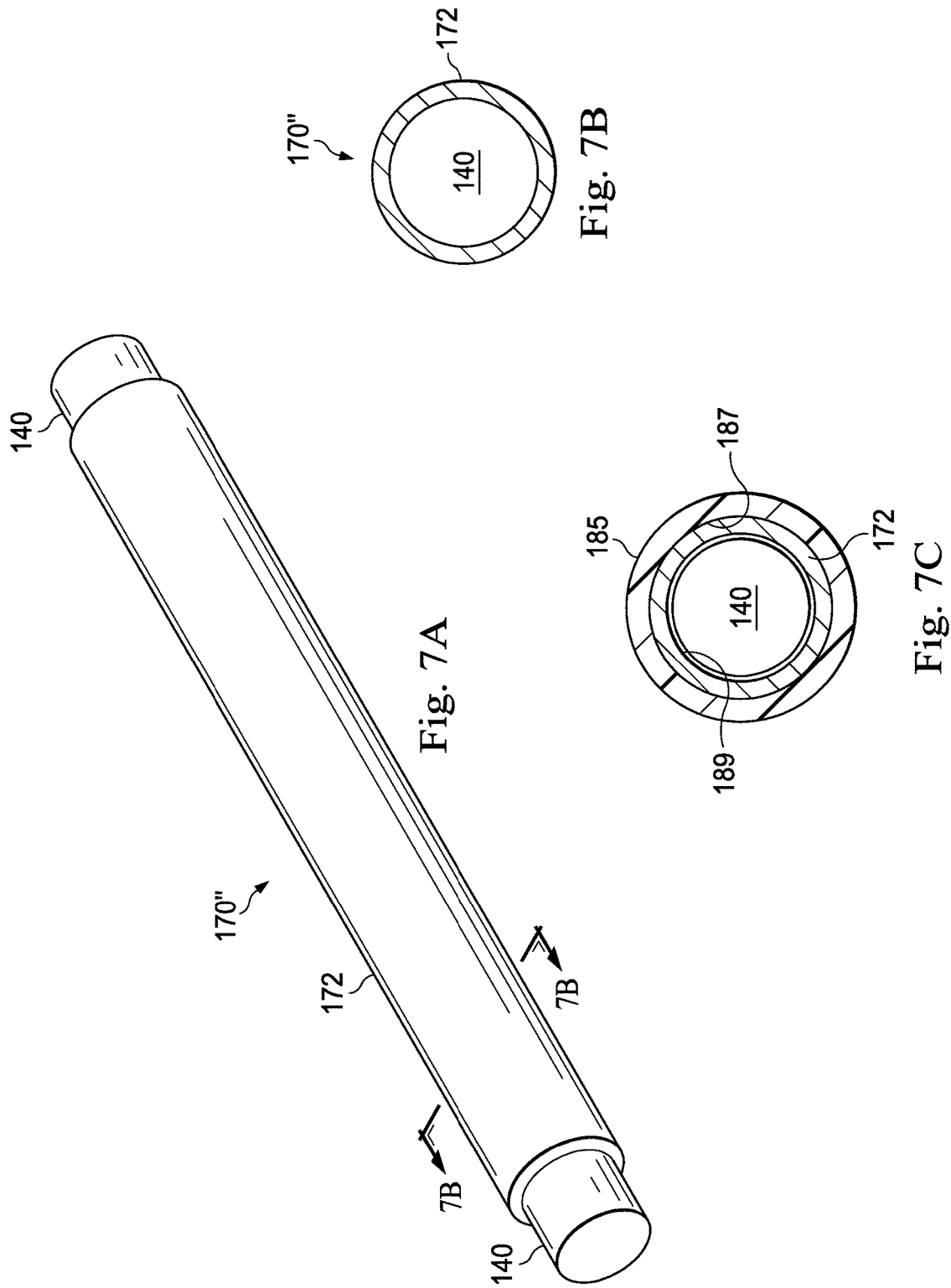

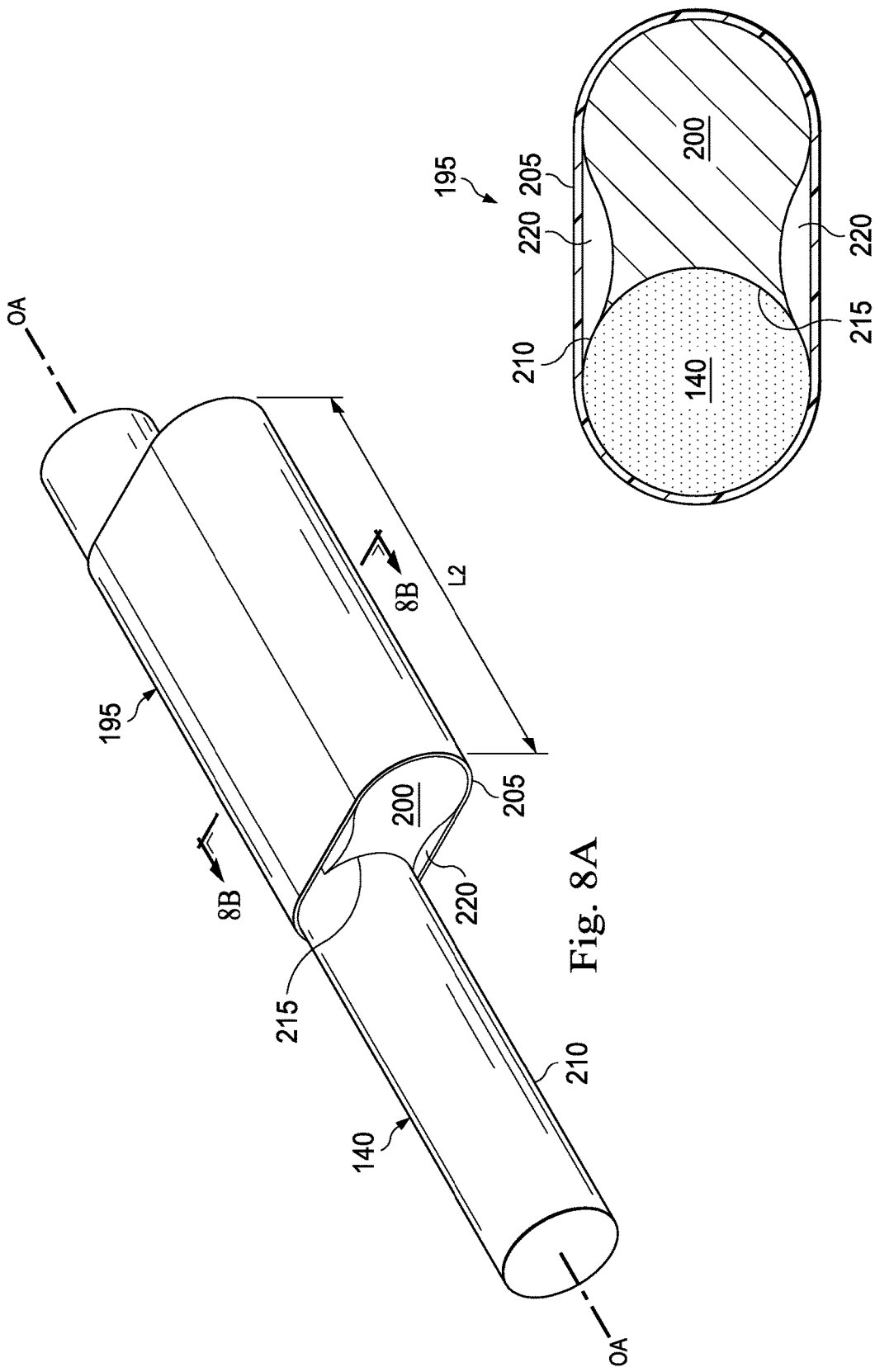

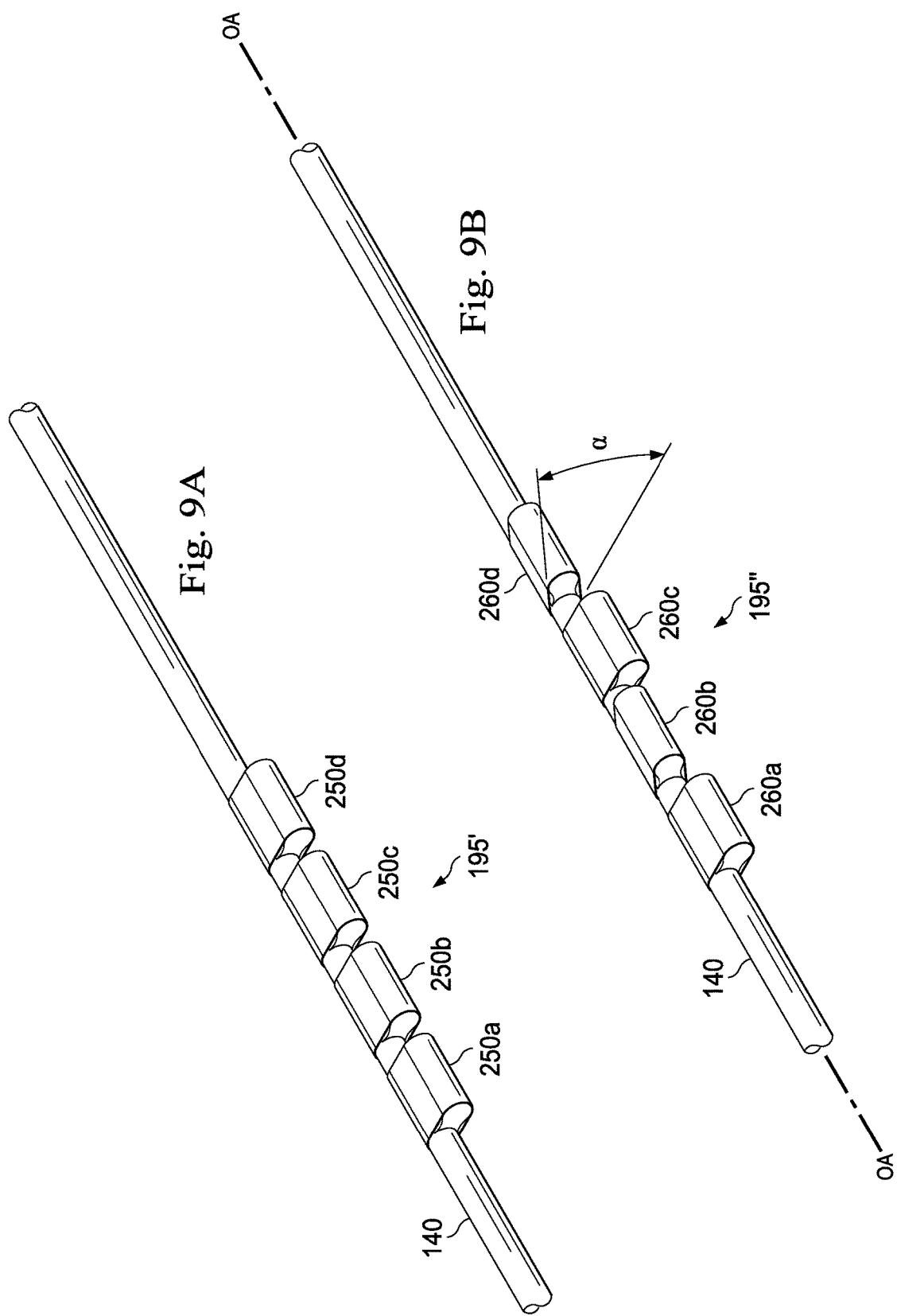

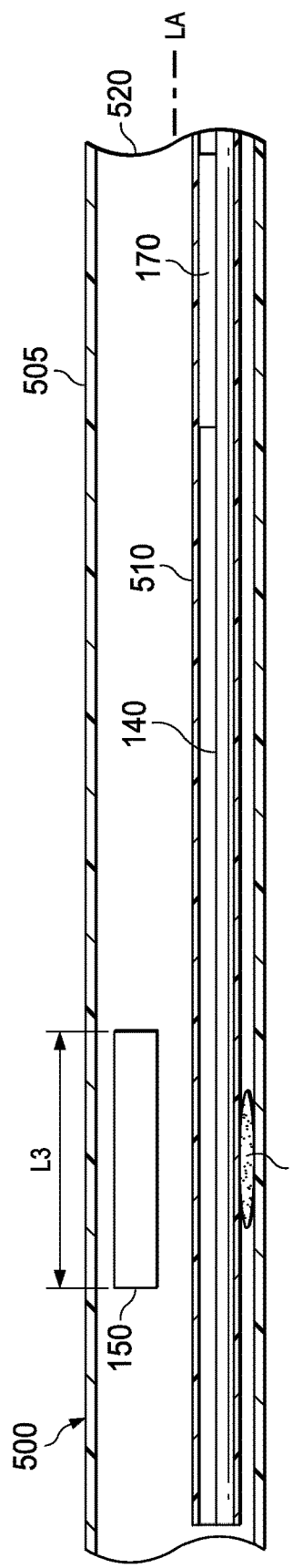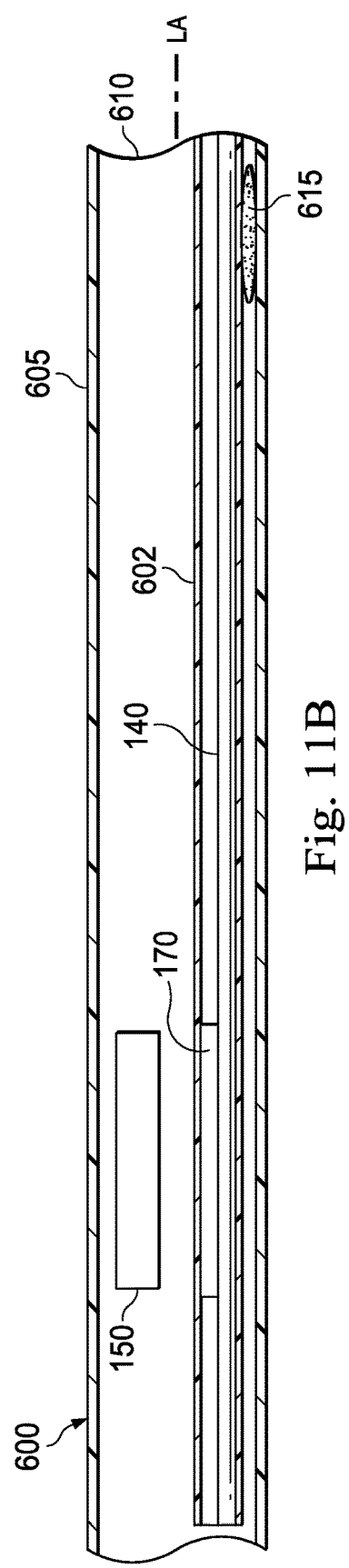
Fig. 11A
Fig. 11B

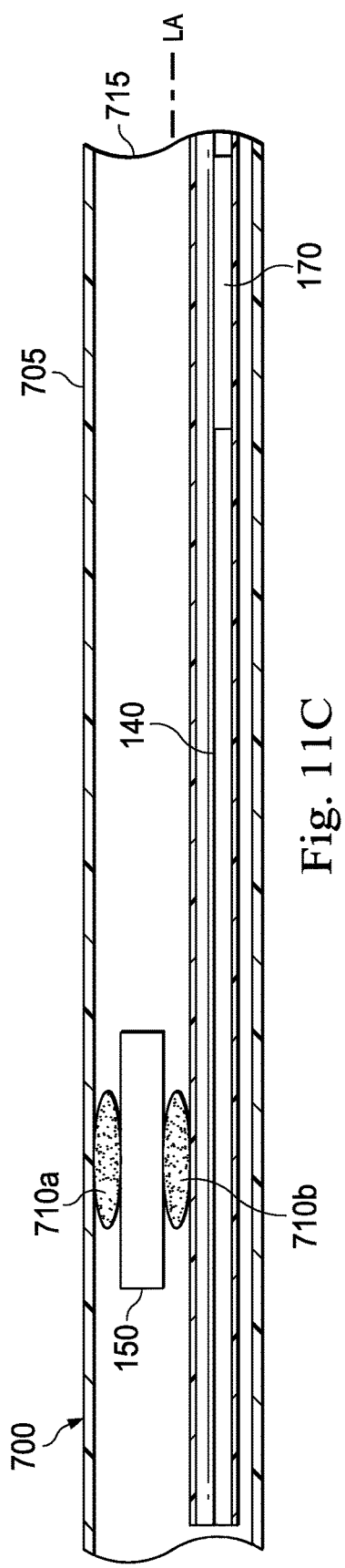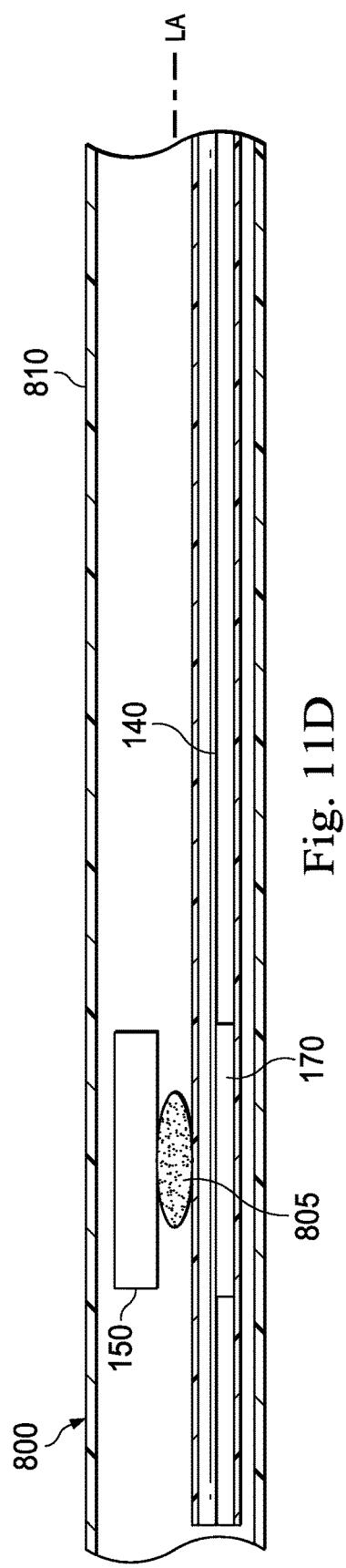

SYSTEMS AND METHODS FOR REDUCING MEASUREMENT ERROR USING OPTICAL FIBER SHAPE SENSORS

RELATED APPLICATIONS

This patent application claims priority to and the benefit of the filing date of U.S. Provisional Patent Application 62/065,349, entitled "SYSTEMS AND METHODS FOR REDUCING MEASUREMENT ERROR USING OPTICAL FIBER SHAPE SENSING," filed Oct. 17, 2014, which is incorporated by reference herein in its entirety.

FIELD

The present disclosure is directed to systems and methods for reducing measurement error in a shape sensing optical fiber, and more particularly to systems and methods for reducing measurement error using shape sensing optical fibers in medical instruments.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert medical instruments to reach a target tissue location. To reach the target tissue location, the minimally invasive medical instruments may navigate natural or surgically created passageways in anatomical systems such as the lungs, the colon, the intestines, the kidneys, the heart, the circulatory system, or the like. Navigational assist systems help the clinician route the medical instruments and avoid damage to the anatomy. These systems can incorporate the use of shape sensors to more accurately describe the shape, position, orientation, and pose of the medical instrument in real space or with respect to pre-procedural or concurrent images. The accuracy and precision of these shape sensors may be compromised by many factors including twisting of the sensor, temperature variations, the location of the shape sensor within the instrument, and axial loading on the sensor.

Improved systems and methods are needed for increasing the accuracy and precision of navigational assist systems, including minimizing the effects of factors that compromise shape sensor accuracy. The devices, systems, and methods disclosed herein overcome one or more of the deficiencies of the prior art.

SUMMARY

The embodiments of the invention are summarized by the claims that follow below.

In one embodiment, an apparatus comprises an instrument including an elongated shaft. The apparatus also comprises a first shape sensor including an elongated optical fiber extending within the elongated shaft at a first radial distance from the neutral axis. The apparatus also comprises a twist resistant feature configured to reduce twisting of the elongated optical fiber relative to the elongated shaft while permitting axial translation of the elongated optical fiber within the elongated shaft.

In another embodiment, a method of operating a shape sensing apparatus comprises providing an instrument including a shape sensor disposed along an elongated shaft and receiving shape data from the shape sensor. The shape sensor includes an elongated optical fiber extending within the elongated shaft and coupled to a twist resistant feature along at least a portion of the elongated optical fiber. The twist resistant feature is configured to limit the twisting of the optical fiber relative to the elongated shaft. The method also comprises generating an instrument bend measurement based upon the received shape data.

In another embodiment, an apparatus comprises an instrument including an elongated shaft and a first shape sensor including an elongated optical fiber extending within the elongated shaft at a first radial distance from the neutral axis. The apparatus also includes a twist mitigation feature configured to reduce axial strain in at least a portion of the first shape sensor.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 6A and 6B illustrate an optical fiber shape sensor and an exemplary twist resistant feature according to an embodiment of the present disclosure. FIG. 6A is a perspective view and FIG. 6B is a cross-sectional view.

FIGS. 7A-7C illustrate an optical fiber shape sensor and an exemplary twist resistant feature according to various embodiments of the present disclosure. FIG. 7A is a perspective view and FIGS. 7B and 7C are cross-sectional views.

FIG. 8A is a perspective view of an optical fiber shape sensor and an exemplary keying feature according an embodiment of the present disclosure.

FIG. 8B is a cross-sectional view of the optical fiber shape sensor and the exemplary keying feature shown in FIG. 8A.

FIG. 9A is a perspective view of an optical fiber shape sensor and an exemplary keying feature according an embodiment of the present disclosure.

FIG. 9B is a perspective view of an optical fiber shape sensor and an exemplary keying feature according an embodiment of the present disclosure.

FIGS. 11A-11D are cross-sectional views of different exemplary medical instruments that each include an optical fiber shape sensor, a twist resistant feature, and a reference sensor according to various embodiments of the present disclosure.

DETAILED DESCRIPTION

Figure 1:
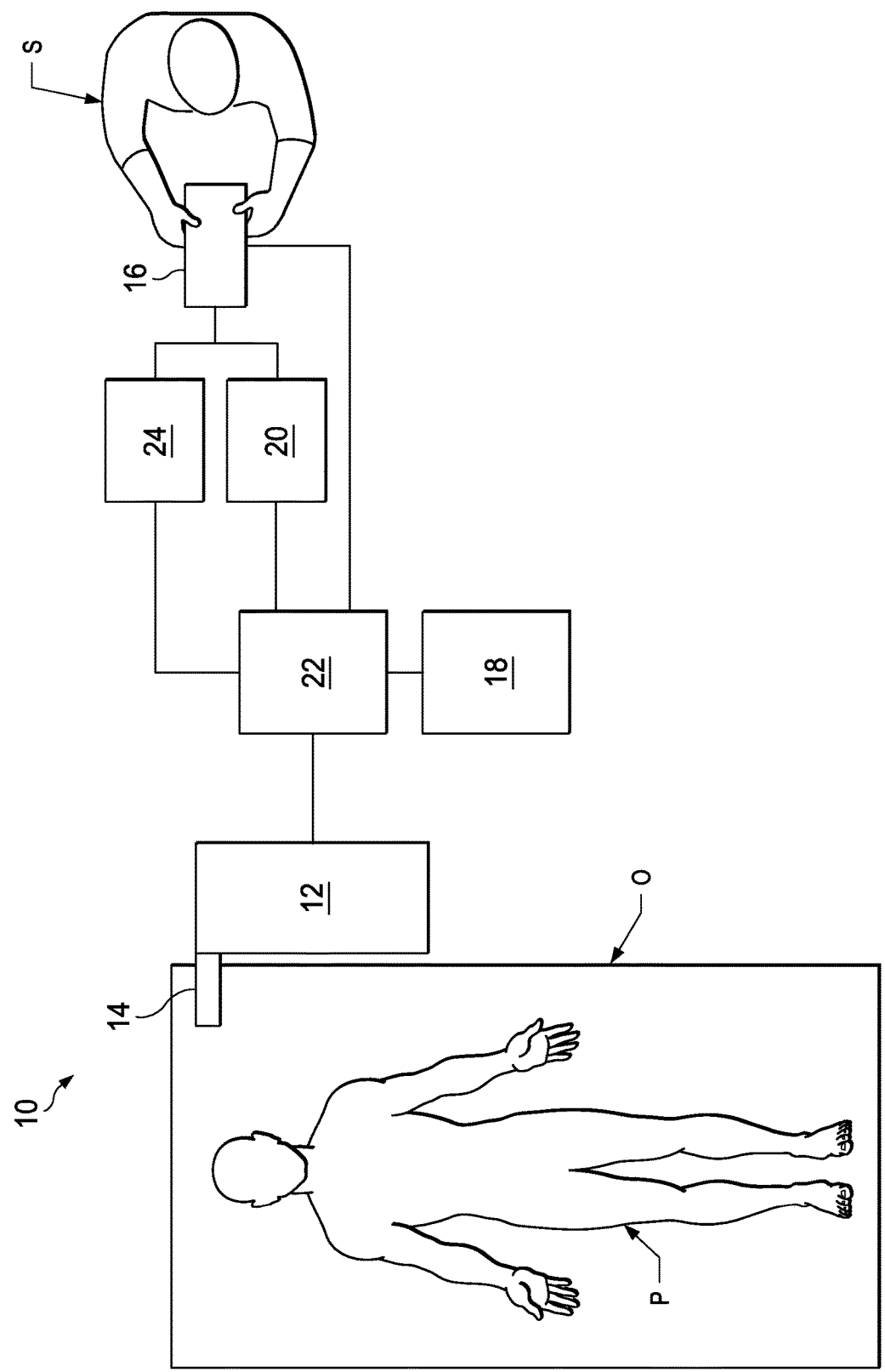
FIG. 1 illustrates an exemplary teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the disclosure.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or process described with respect to one embodiment may be combined with the features, components, and/or process described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, medical instruments are used in many orientations and positions, and there terms are not intended to be limiting and absolute.

The present disclosure relates generally to using shape sensor systems to monitor, estimate, and/or predict the shape and/or position of medical instruments used in a variety of medical procedures, including without limitation diagnostic, surgical, and/or therapeutic procedures. In particular, in some embodiments, the shape sensor systems disclosed herein rely on the ability to obtain and interpret optical data from optical shape sensor fibers coupled to a flexible body of a medical instrument. In particular, some embodiments of the present disclosure are related to shape and/or position tracking by minimizing the effect of twist on the optical fiber while the operator uses the medical instrument during a minimally invasive procedure. In some embodiments, the shape sensing systems may be coupled to a teleoperational medical system. The embodiments disclosed herein may improve the positional and shape assessment abilities of shape sensing systems coupled to teleoperational medical systems by reducing the errors and inaccuracies introduced by twisting of the optical fibers during manipulation of the medical instruments. In particular, some embodiments described herein utilize mechanical elements such as, by way of non-limiting example, splines and adhesive to constrain the movement of the optical fiber in relation to the body of the medical instrument. For example, in some embodiments, the optical fiber is coupled to various points and/or other sensors (e.g., an EM positional sensor) within the medical instrument to minimize the effect of twist on the optical fiber.

Those of skill in the art will realize that the shape sensing systems disclosed herein may be utilized in similar (e.g., non-teleoperational) applications benefiting from more accurate shape and/or position sensing. By utilizing the shape sensing systems and methods disclosed herein, a user may experience more intuitive and more efficient interaction with the medical instruments and other components coupled to a teleoperational medical system.

According to various embodiments, minimally invasive medical procedures may be performed using a teleoperational system to guide instrument delivery and operation. Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 10 generally includes a teleoperational assembly 12 near or mounted to an operating table O on which a patient P is positioned. The teleoperational assembly 12 may be referred to as a patient-side manipulator (PSM). A medical instrument system 14 is operably coupled to the teleoperational assembly 12. An operator input system 16 allows a surgeon or other type of clinician S to view images of or representing the surgical site and to control the operation of the medical instrument system 14. The operator input system 16 may be referred to as a master or surgeon's console. One example of a teleoperational surgical system that can be used to implement the systems and techniques described in this disclosure is a da Vinci® Surgical System manufactured by Intuitive Surgical, Inc. of Sunnyvale, Calif.

The teleoperational assembly 12 supports the medical instrument system 14 and may include a kinematic structure of one or more non-servo controlled links (e.g., one or more links that may be manually positioned and locked in place, generally referred to as a set-up structure) and a teleoperational manipulator. The teleoperational assembly 12 includes plurality of motors that drive inputs on the medical instrument system 14. These motors move in response to commands from a control system 22. The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument.

The teleoperational medical system 10 also includes an image capture system 18 which includes an image capture or imaging device, such as an endoscope, and related image processing hardware and software. The imaging device may be integrally or removably coupled to the medical instrument system 14. Additionally or alternatively, a separate imaging device that is attached to a separate manipulator assembly may be used with the medical instrument system to image the surgical site.

The teleoperational medical system 10 also includes a control system 22 that is operatively linked to sensors, motors, actuators, and other components of the teleoperational assembly 12, the operator input system 16, and the image capture system 18. The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. More specifically, in response to the surgeon's input commands, the control system 22 effects servomechanical movement medical instrument system 14. The control device(s) may include one or more of any number of a variety of input devices, such as hand grips, joysticks, trackballs, data gloves, trigger-guns, hand-operated controllers, foot-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The system operator sees images, captured by the image capture system 18, presented for viewing on a display system 20 operatively coupled to or incorporated into the operator input system 16. The display system 20 displays an image or representation of the surgical site and medical instrument system(s) 14 generated by sub-systems of the image capture system 18. The display system 20 and the operator input system 16 may be oriented so the operator can control the medical instrument system 14 and the operator input system 16 with the perception of telepresence. The display system 20 may include multiple displays such as separate right and left displays for presenting separate images to each eye of the operator, thus allowing the operator to view stereo images.

Alternatively or additionally, display system 20 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intraoperative images may include two-dimensional, three-dimensional, or four-dimensional (including e.g., time based or velocity based information) images and associated image data sets for reproducing the images. The image may be, for example, a two dimensional (2D) or three dimensional (3D) image captured by an imaging device such as an endoscope positioned within the surgical site. In some embodiments, the display system 20 may display a virtual navigational image in which the actual location of a medical instrument is dynamically referenced with preoperative images to present the surgeon S with a virtual image of a surgical site at the location of the tip of the medical instrument. An image of the tip of the medical instrument or other graphical or alphanumeric indicators may be superimposed on the virtual image to assist the surgeon controlling the medical instrument. The display system 20 may be implemented as hardware, firmware, software, or a combination thereof which interact with or are otherwise executed by one or more computer processors, which may include the processors of the control system 22.

The control system 22 includes at least one memory and at least one processor (not shown), and typically a plurality of processors, for effecting control between the teleoperational system 12, the medical instrument system 14, the operator input system 16, the image capture system 18, and the display system 20. The control system 22 also includes programmed instructions (e.g., a computer-readable medium storing the instructions) to implement some or all of the methods described in accordance with aspects disclosed herein. While the control system 22 is shown as a single block in the simplified schematic of FIG. 1, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system 22 supports wireless communication protocols such as Bluetooth, IrDA, HomeRF, IEEE 802.11, DECT, and Wireless Telemetry.

In some embodiments, the control system 22 may include one or more servo controllers that receive force and/or torque feedback from the medical instrument system 104. Responsive to the feedback, the servo controllers transmit signals to the operator input system 16. The servo controller(s) may also transmit signals instructing the teleoperational assembly 12 to move the medical instrument system(s) 14 which extend into an internal surgical site within the patient body via openings in the body. Any suitable conventional or specialized servo controller may be used. A servo controller may be separate from, or integrated with, the teleoperational assembly 12. In some embodiments, the servo controller and the teleoperational assembly are provided as part of a teleoperational arm cart positioned adjacent to the patient's body.

The teleoperational medical system 10 may further include optional operation and support systems 24 such as illumination systems, eye tracking systems, steering control systems, irrigation systems, and/or suction systems. These systems may be operatively coupled to or incorporated into the operator input system 16. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
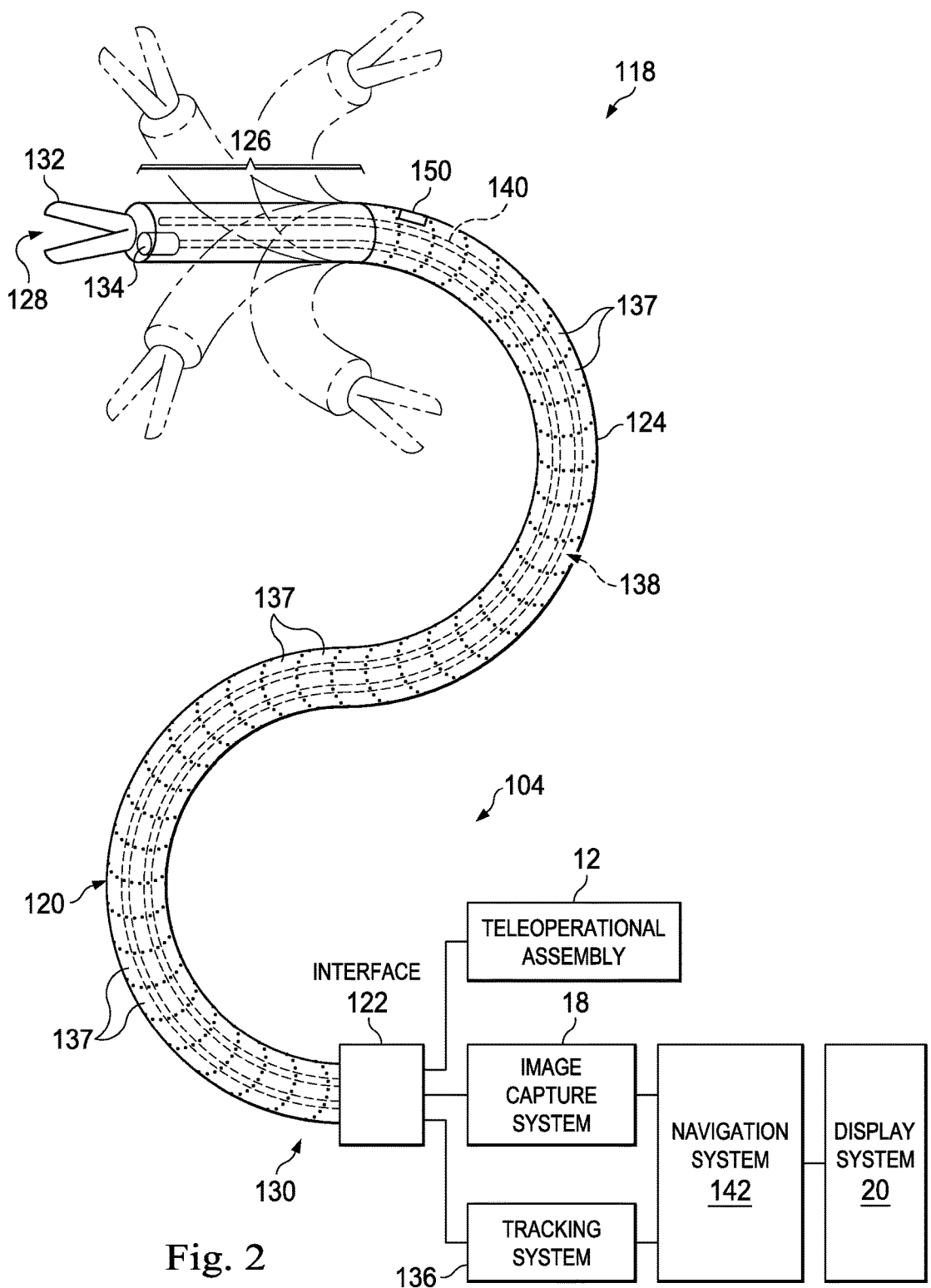
FIG. 2 illustrates a medical instrument system utilizing aspects of the teleoperational medical system according to one embodiment of the present disclosure.

FIG. 2 illustrates a shape sensing apparatus 118 which includes the medical instrument system 14 and its interfacing systems. The medical instrument system 14 includes a steerable instrument 120 coupled by an interface 122 to the teleoperational assembly 12 and the image capture system 18. In the embodiment of FIG. 2, the instrument 118 is teleoperated within the teleoperational surgical system 10. In an alternative embodiment, the teleoperational assembly 12 may be replaced by direct operator control. In the direct operation alternative, various handles and operator interfaces may be included for hand-held operation of the instrument.

The instrument 120 has a flexible body 124 (e.g. a cannula), a steerable tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The end effector is a working distal part that is manipulable for a medical function, e.g., for effecting a predetermined treatment of a target tissue. For instance, some end effectors have a single working member such as a scalpel, a blade, or an electrode. Other end effectors such as the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which medical instruments can be deployed and used at a target surgical location.

The instrument 120 can also include an image capture element 134 which may include a stereoscopic or monoscopic camera disposed at the distal end 128 for capturing images that are transmitted to and processed by the image capture system 18 for display by the display system 20. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

A tracking system 136 interfaces with a sensor system 138 for determining the shape (and optionally, pose) of the distal end 128 and or one or more segments 137 along the instrument 120. Although only an exemplary set of segments 137 are depicted in FIG. 2, the entire length of the instrument 120, between the distal end 128 and the proximal end 130 and including the tip 126 may be effectively divided into segments, the shape (and location, pose, and/or position) of which may be determined by the sensor system 138. The tracking system 136 may be implemented as hardware, firmware, software or a combination thereof which interact with or are otherwise executed by one or more computer processors, which may include the processors of the control system 22.

The sensor system 138 includes an optical fiber shape sensor 140 aligned with the flexible body 124 (e.g., provided within an interior channel (not shown) or mounted externally). The tracking system 136 is coupled to a proximal end of the optical fiber shape sensor 140. In this embodiment, the optical fiber shape sensor 140 has a diameter of approximately 200 μm. In other embodiments, the dimensions may be larger or smaller.

The optical fiber shape sensor 140 forms a fiber optic bend sensor for determining the shape of the instrument 120. In one example, optical fibers including Fiber Bragg Gratings (FBG) are used to provide strain measurements in structures in one or more dimensions. Various systems and methods for monitoring the shape and relative position of an optical fiber in three dimensions are described in U.S. Patent Application Publication No. 2006/0013523, filed on Jul. 13, 2005, U.S. provisional Patent Application Ser. No. 60/588,336, filed on Jul. 16, 2004, and U.S. Pat. No. 6,389,187, filed on Jun. 17, 1998, the disclosures of which are incorporated herein in their entireties. In other alternatives, sensors employing other strain sensing techniques such as Rayleigh scattering, Raman scattering, Brillouin scattering, and Fluorescence scattering may be suitable. In other alternative embodiments, the shape of the instrument 120 may be determined using other techniques. For example, if the history of the instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument.

The optical fiber shape sensor 140 is used to monitor the shape of at least a portion of the instrument 120. More specifically, light passing through the optical fiber shape sensor 140 is processed by the tracking system 136 for detecting the shape of the medical instrument 120 and for utilizing that information to assist in surgical procedures. The tracking system 136 may include a detection system for generating and detecting the light used for determining the shape of the instrument 120. This information, in turn, in can be used to determine other related variables, such as velocity and acceleration of the parts of a medical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

The information from the tracking system 136 may be sent to a navigation system 142 where it is combined with information from the image capture system 18 and/or the preoperatively taken images to provide the surgeon or other operator with real-time position information on the display system 20 for use in the control of the instrument 120. The navigation system 142 may be part of the control system 22 shown in FIG. 1. Alternatively, the navigation system 142 may be part of the optional systems 24 shown in FIG. 1. The navigation system 142 and/or the control system 22 may utilize the position information as feedback for positioning the instrument 120. Various systems for using fiber optic sensors to register and display a medical instrument with surgical images are provided in U.S. patent application Ser. No. 13/107,562, entitled "Medical System Providing Dynamic Registration of a Model of an Anatomical Structure for Image-Guided Surgery," which is incorporated by reference herein in its entirety.

In some embodiments, a series of positional sensors, such as electromagnetic (EM) sensors, positioned along the instrument can additionally or alternatively be used for shape sensing. A history of data from a positional sensor, such as an EM sensor, on the instrument during a procedure may be used to represent the shape of the instrument, particularly if an anatomical passageway is generally static. For example, in the pictured embodiment, the instrument 118 includes a position sensor 150 (e.g., an electromagnetic (EM) sensor system) which may be disabled by an operator or an automated system (e.g., a function of the control system 22) if it becomes unreliable due to, for example, magnetic interference from other equipment in the surgical suite or if other navigation tracking systems are more reliable. The position sensor 150 may be an EM sensor system that includes one or more conductive coils that may be subjected to an externally generated electromagnetic field. Each coil of the EM sensor system 150 then produces an induced electrical signal having characteristics that depend on the position and orientation of the coil relative to the externally generated electromagnetic field. In one embodiment, the EM sensor system may be configured and positioned to measure six degrees of freedom ("6-DOF"), e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety. In the pictured embodiment, the position sensor 150 is shown positioned within the body 124 near the distal end 128 of the instrument 118. In other embodiments, the position sensor 150 may be positioned at any of a variety of locations along, inside, or outside of the instrument 118.

In some embodiments, alternatively or additionally, a wireless device with position or orientation controlled by an external magnetic field may be used for shape sensing. The history of its position may be used to determine a shape for the navigated passageways.

Figure 3:
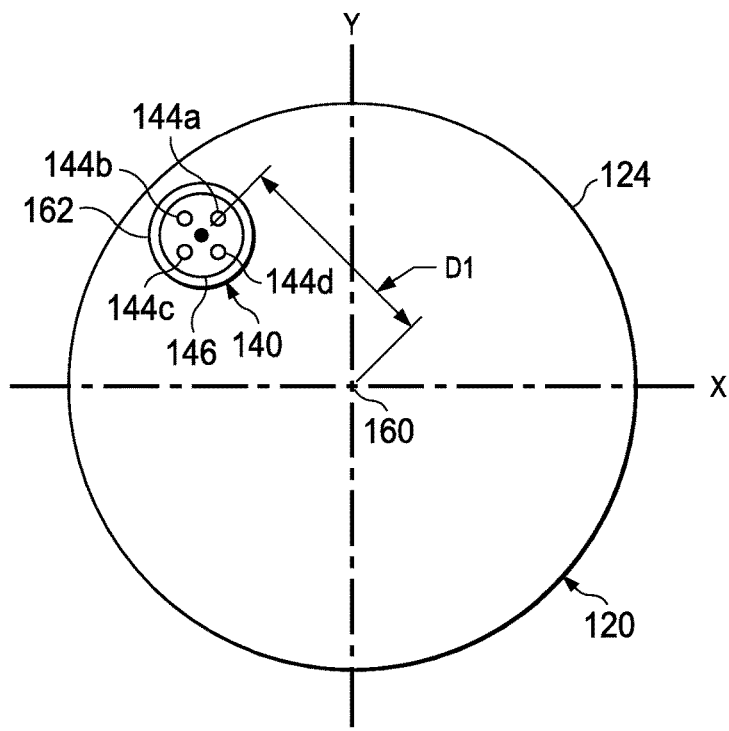
FIGS. 3 and 4 are cross-sectional views of a medical instrument including an optical fiber shape sensor according to one embodiment of the present disclosure.
Figure 4:
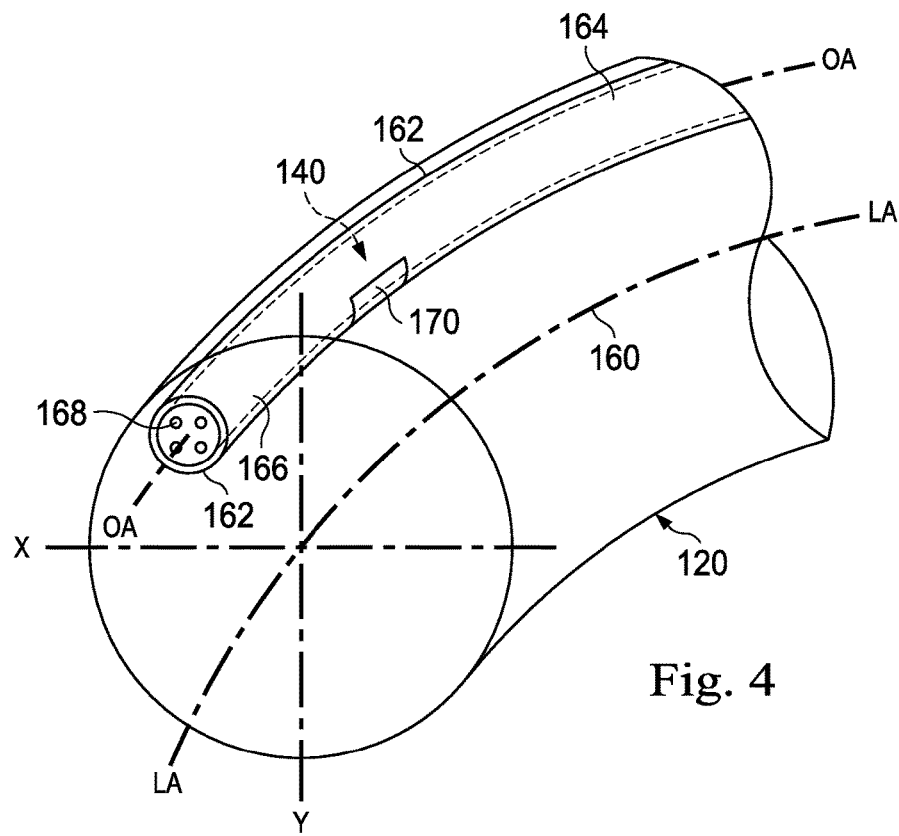

FIGS. 3 and 4 are cross-sectional views of the medical instrument 120 including the optical fiber shape sensor 140 according to one embodiment of the present disclosure. To simplify the illustration, details of the steering components and visual imaging system have been omitted. The illustration is not drawn to scale. In this embodiment, the optical fiber shape sensor 140 comprises four cores 144a-144d contained within a single cladding 146. Each core may be single-mode with sufficient distance and cladding separating the cores such that the light in each core does not interact significantly with the light carried in other cores. In other embodiments, the number of cores may vary or each core may be contained in a separate optical fiber. In the embodiments of FIGS. 3 and 4, the fiber cores are arranged with 90° spacing about the center of the optical fiber shape sensor 140. In other embodiments, four cores may be arranged with one core in the center of the fiber and three cores spaced at 120° intervals about the center.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBGs, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, which is incorporated by reference herein in its entirety.

The shape sensor may provide shape data to the tracking system 136 shown in FIG. 2 in the form of strain data. Additionally, strain data may be supplemented with data related to twist errors, light response, temperature errors, or other data that may contribute to determining shape. When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local bend radius of the fiber, the radial position of the core with respect to the fiber centerline and the angular position of the core about the core centerline with respect to the plane of fiber bending. For example, strain induced wavelength shifts in regions of the cores containing FBGs located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

In the embodiment shown in FIGS. 3 and 4, the optical fiber shape sensor 140 includes the four optical cores 144a-144d disposed at equal radial distances from and equal angular intervals about the axis of the optical fiber shape sensor 140 such that in cross-section, opposing pairs of cores 144a-144c and 144b-144d form orthogonal axes. The sensing locations along the four optical cores are aligned such that measurements from each core are from substantially correlated axial regions along the optical fiber. The fiber cores 144 may include multiple FBGs or sets thereof that are axially distributed along each core 144a-144d. In various embodiments, the FBGs may be continuous, overlapping or partially overlapping. For example, in one embodiment, each core 144a-144d includes an array of collinear FBGs that are disposed at known positions along the lengths of each core 144a-144d such that the FBGs 144a-d for all four cores 144a-144d are longitudinally aligned (e.g., with respect to distance from the distal end 128 of the medical instrument 120) at a plurality of sensor segments 137, including the steerable tip 126.

A bending of the optical fiber shape sensor 140 in one of the sensor segments 137 will lengthen at least one core 144a-144d with respect to the opposing core 144a-144d. Interrogation of this length differential along the fiber enables the angle and radius of bending to be extracted. This interrogation may be performed using the tracking system 136. There are a variety of ways of multiplexing the FBG's so that a single fiber core can carry many sensors and the readings of each sensor can be distinguished. Some of the various ways are described in U.S. patent application Ser. No. 13/049,012, which is incorporated by reference herein in its entirety.

In alternative embodiments, fibers with fewer or more cores may be used. Likewise, the fiber cores may be arranged in different patterns, such as, a central core with (axial refers to the fiber orientation, not the spacing) additional cores spaced at angular intervals around the central core. In one embodiment, a hollow utility channel may provide access for removable devices including removable medical instruments, removable steering components, removable visualization components or the like. In some embodiments, the instrument body 124 may include an internal channel or fiber lumen sized to accommodate the optical fiber 140 and separate it from the steering or visualization components, which themselves may be accommodated through separate channels. In FIGS. 3 and 4, for example, the optical fiber shape sensor 140 is positioned within a fiber lumen 162. The fiber lumen 162 may extend throughout the length of the medical instrument 120.

In FIG. 3, the optical fiber shape sensor 140 is centered at a radial distance D1 from a neutral axis 160 that in this embodiment extends longitudinally through the instrument 120 along a longitudinal axis LA of the instrument. The neutral axis 160 is the axis of the instrument 120 along which little or no axial strains (due to tension, twist, or compression) occur during bending. In other embodiments, the optical fiber shape sensor 140 may be positioned at or along the neutral axis 160. In alternative embodiments, the optical fiber shape sensor 140 (and the fiber lumen 162) may be centered about the neutral axis 160 or located at a different radial distance. In this embodiment, the optical fiber shape sensor 140 may be offset from the neutral axis 160 to accommodate other components of the instrument 120 such as cables or other steering components or visualization components (not shown) that may be centered on or clustered about the neutral axis 160. In this embodiment, the neutral axis 160 extends generally along the central axis of the instrument 120. In alternative embodiments, the optical fiber shape sensor 140 may be positioned within the instrument 120 (e.g., within the fiber lumen 162) at other distances from the neutral axis or at other angular displacements from the neutral axis.

When the optical fiber shape sensor 140 is positioned offset from the neutral axis, the optical fiber shape sensor 140 is subject to axial tensile and compressive forces during bending which strain all of the fiber cores and may contribute to bending measurement error. Twist in the optical fiber shape sensor 140 may cause strain or stress on the optical fiber shape sensor 140 (e.g., in addition to the strain caused by the bending of the medical instrument 120) that contributes to bending measurement error. Twist in the optical fiber shape sensor 140 may result, for example, from the twisting or rotational displacement of the medical instrument 120 as the medical instrument is steered or guided in multiple directions. Twist in the optical fiber shape sensor occurs when a proximal portion 164 of the optical fiber shape sensor 140 is rotated about a longitudinal axis OA of the optical fiber shape sensor 140 relative to a distal portion 166 of the optical fiber shape sensor 140. For example, an optical core 168 may be located at different radial angles with respect to the longitudinal axis OA in the distal position 166 and the proximal portion 164. Because the strain on the optical fiber shape sensor 140 due to axial forces may not be distinguishable from the apparent strain induced by twist, it may be difficult to determine the magnitude of the bending measurement error due to axial forces versus twist. Unless the data from the FBGs can be parsed into identifiable components of reflected optical readings from stress or strain due to bending and reflected optical readings from stress or strain due to twist or torsion, the displacement information determined from the optical data can include inaccuracy or error in estimating the position or shape of the medical instrument 120.

Accordingly, in order to accurately estimate or predict the position or shape of the elongate medical instrument 120 as discussed above using the optical fiber 120, it may be necessary to reduce the potential of twist or rotation of the optical fiber 120 during manipulation (e.g., steering and/or bending) of the medical instrument 120. In some embodiments described herein, the optical fiber shape sensor 140 is mechanically constrained to prevent or reduce twisting of the proximal portion 164 relative to the distal portion 166 of the optical fiber shape sensor 140 while permitting axial translation along a longitudinal axis through the medical instrument 120 (e.g., parallel to the longitudinal axis LA). In some instances, the optical fiber shape sensor 140 is mechanically prevented from or limited in twisting about the longitudinal axis OA by a twist resistant feature 170.

Figure 5:
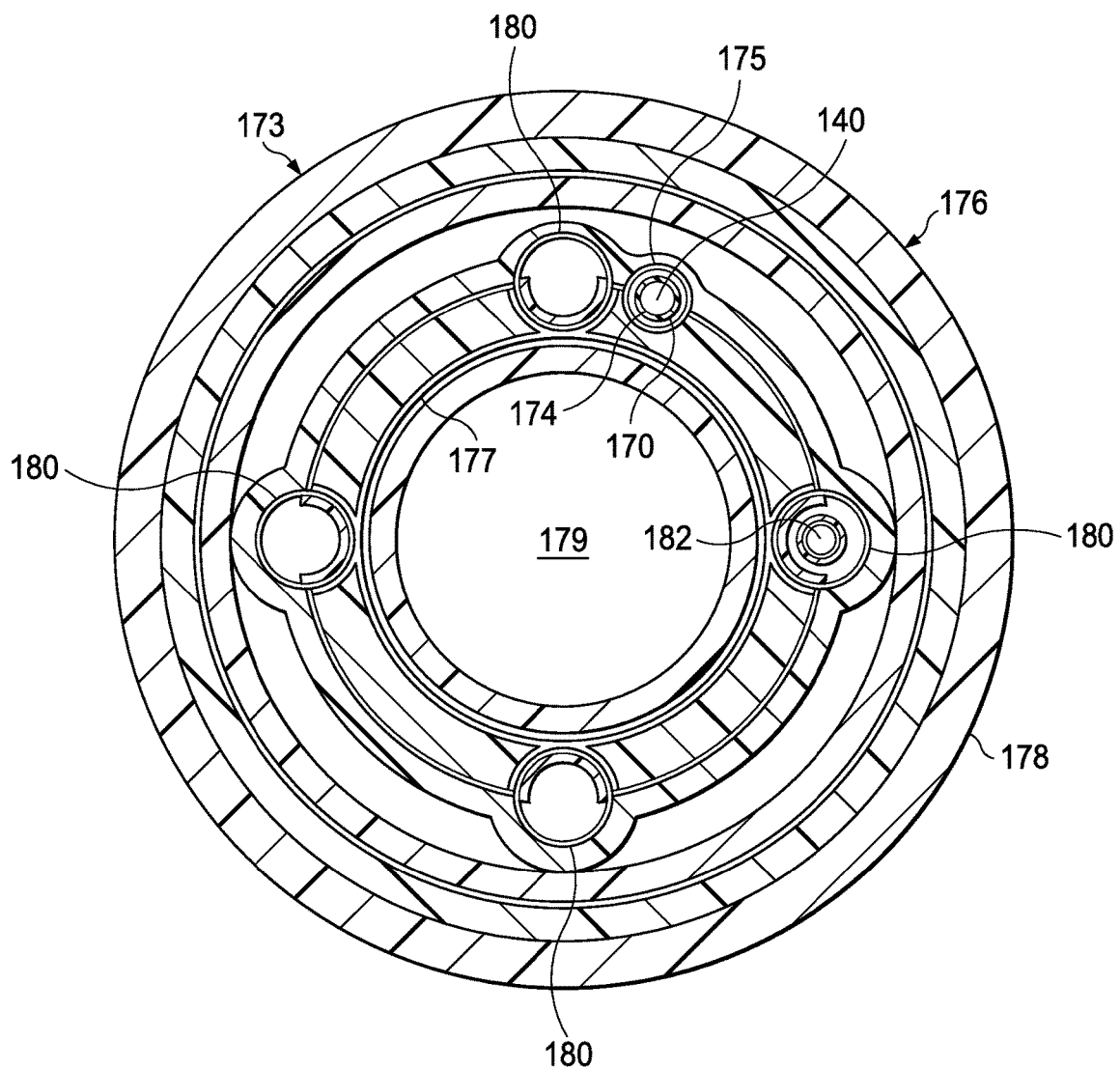
FIG. 5 illustrates a cross-sectional view of an exemplary medical instrument including a fiber lumen containing an optical fiber shape sensor and an exemplary twist resistant feature according to an embodiment of the present disclosure.

For example, FIG. 5 illustrates a cross-sectional view of an exemplary twist resistant feature 170 associated with an exemplary medical instrument 173 including an optical fiber shape sensor extending within a fiber lumen 175 according to an embodiment of the present disclosure. The medical instrument 173 may be the same as the medical instrument 120 shown in FIG. 2. In the pictured embodiment, the twist resistant feature 170 is disposed between the optical fiber shape sensor 140 and a luminal wall 174 of the fiber lumen 175. The twist resistant feature 170 may comprise any of a variety of mechanical elements configured to minimize or prevent the twisting of the optical fiber shape sensor 140, including features of the optical fiber shape sensor 140 itself, features of the fiber lumen 175, and independent features such as, by way of non-limiting example, coatings, sheaths, and key features.

In the pictured embodiment, the fiber lumen 175 comprises a hollow, tubular space formed within a body 176 of the instrument 173. The body 176 forms an elongate, flexible tube having an inner surface 177 and an outer surface 178. The inner surface 177 of the body 176 defines a central lumen 179. The central lumen 179 may comprise the working channel of the medical instrument 173. The medical instrument 173 includes a plurality of actuation channels 180 extending within the body 176 that are configured to receive actuation cables 182.

In alternative embodiments, the optical fiber shape sensor 140 can be coupled, bonded, or attached to the inner surface 177 or to the outer surface 178 as appropriate. In still other alternative embodiments, the inner surface 177 may also define a groove in which the optical fiber shape sensor 140 may be positioned. In yet other embodiments, the optical fiber shape sensor 140 can be coupled to or integral with the outer surface 178 using, for example, a suitable adhesive or bonding agent, and/or the optical fiber shape sensor 140 may be positioned within an aperture or groove that is formed within the outer surface 178. Further, the optical fiber 140 can be coupled to the instrument 173 in such a manner that a portion of the optical fiber 140 is coupled at a known reference location on a proximal portion of the instrument 173.

FIGS. 6A and 6B illustrate the optical fiber shape sensor 140 coupled to an exemplary twist resistant feature 170' according to one embodiment of the present disclosure. FIG. 6A illustrates a perspective view of the optical fiber shape sensor 140 and the twist resistant feature 170', and FIG. 6B illustrates a cross-sectional view across line 6B-6B in FIG. 6A of the optical fiber shape sensor 140 and the twist resistant feature 170'. In some embodiments, as shown in FIGS. 6A and 6B, the twist resistant feature 170' comprises a twist resistant sheath or covering 171, such as, by way of non-limiting example, a hypotube or a braided sheath, that is coupled to at least a portion of the optical fiber shape sensor 140. Such a sheath 171 may create friction, limiting twisting movement between the shape sensor 140 and the fiber lumen 175. Thus, the sheath 171 causes the shape sensor 140 to resist twisting within the fiber lumen 175 along at least a part of the length of the medical instrument 120. In alternative embodiments, the twist resistant feature 170' may be a textured surface of the fiber lumen 175 that limits twisting of the shape sensor 140. In still other alternatives, the texture of the sheath 171 or the lumen 175 may be selected to create greater resistance to twisting motion than to axial sliding motion. In alternative embodiments, the sheath 171 may include a structural configuration that inherently resists twist, thereby reducing the twisting of the optical fiber shape sensor 140 coupled to it.

Alternatively, as shown in FIGS. 7A-7C, a twist resistant feature 170" may comprise a coating 172 made from material having a relatively low coefficient of friction, such as, by way of non-limiting example, a Teflon coating, lubricant coating, or polymeric coating. By lowering the coefficient of friction between the optical fiber shape sensor 140 and the walls of the fiber lumen (e.g., the fiber lumen 175 shown in FIG. 5), the coating 172 may facilitate the free rotation of the optical fiber shape sensor 140 (e.g., of both the proximal portion 164 and distal portion 166 of the optical fiber shape sensor 140) within the fiber lumen 175 as the medical instrument is curved, bent, and twisted during use.

FIGS. 7A and 7B illustrate the optical fiber shape sensor 140 surrounded by the coating 172 along at least a portion of its length L1. FIG. 7A illustrates a perspective view of the optical fiber shape sensor 140 and the twist resistant feature 170", and FIG. 7B illustrates a cross-sectional view across line 7B-7B in FIG. 7A of the optical fiber shape sensor 140 and the twist resistant feature 170". In other embodiments, instead of the coating 172 being coupled to the optical fiber shape sensor 140, the coating 172 is coupled to the fiber lumen. FIG. 7C illustrates a cross-sectional view of an exemplary fiber lumen 185 coated along at least a portion of its length with the coating 172. In the pictured embodiment, the fiber lumen 185 includes an inner wall 187, and the coating 172 covers or coats the inner wall 187 along at least a portion of the length of the fiber lumen 185. The optical fiber shape sensor 140 is shown extending within a central lumen 189 of the fiber lumen 185.

Figure 8C:
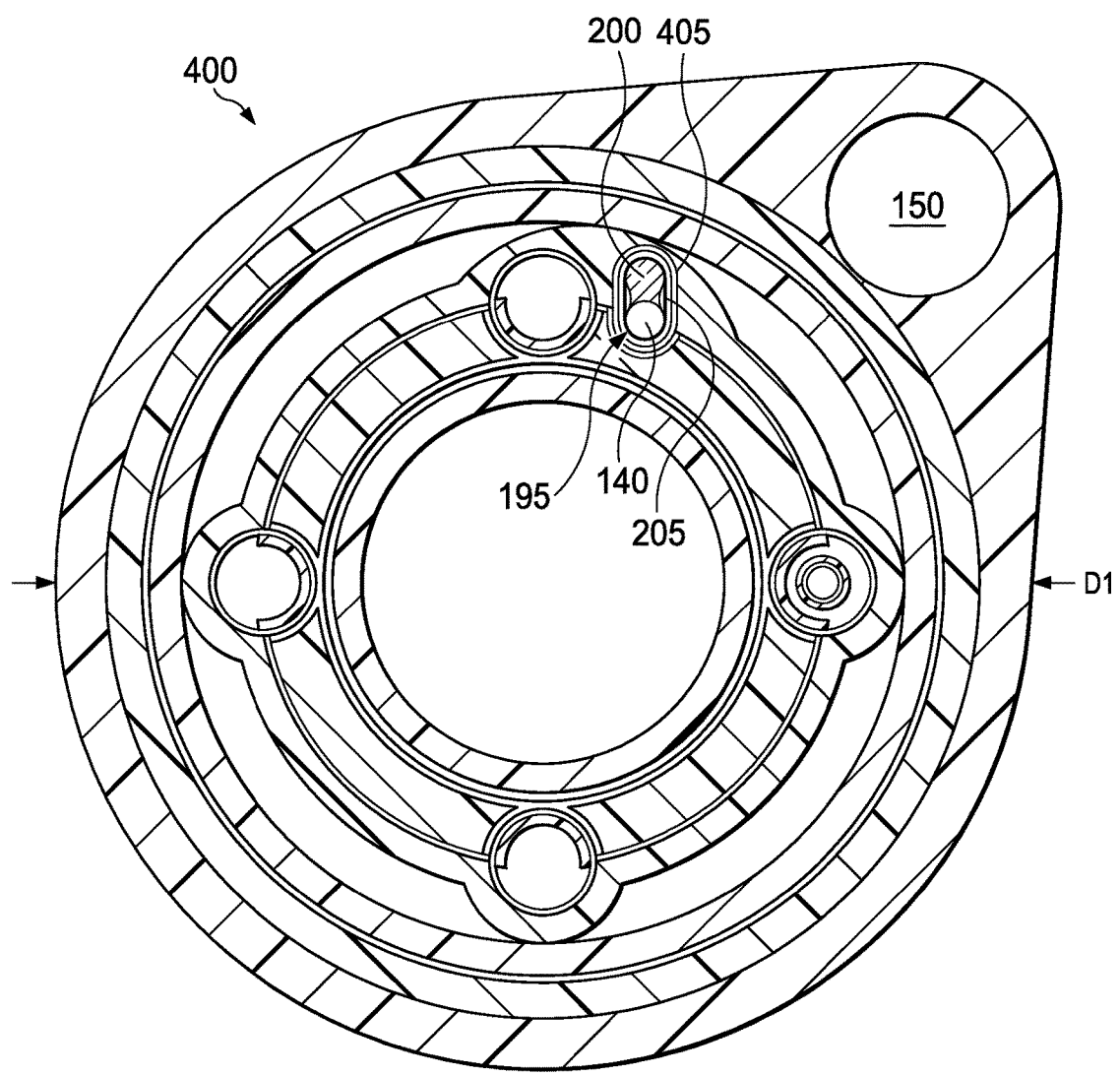
FIG. 8C is a cross-sectional view of an exemplary medical instrument including an optical fiber shape sensor and an exemplary keying feature positioned within an exemplary fiber lumen and a reference sensor according to an embodiment of the present disclosure.

Additionally or alternatively, as shown in FIGS. 8A, 8B, and 8C, a twist resistant feature comprises a keying feature 195 extending along at least a portion of the length of the optical fiber shape sensor 140 and configured to limit the twisting of the optical fiber shape sensor about the longitudinal axis OA. FIGS. 8A and 8B illustrate the optical fiber shape sensor 140 coupled to the keying feature 195. FIG. 8A illustrates a perspective view of the optical fiber shape sensor 140 and the keying feature 195, and FIG. 8B illustrates a cross-sectional view across line 8B-8B in FIG. 8A of the optical fiber shape sensor 140 and the keying feature 195. The keying feature 195 includes a spline 200 coupled to shape sensor 140. The spline 200 may include a length of metal wire, polymeric rod, glass fiber, or other suitable rigid or semi-rigid member. The spline 200 may be cylindrical in shape or may include elongated flat or curved surfaces. The spline 200 may be fixed to the shape sensor 140 with adhesive and/or other mechanical coupling or binding such as a spline sheath 205. The spline 200 mates with an outer surface 210 of the optical fiber shape sensor 140 to limit the rotation or twist of the optical fiber shape sensor 140 at least at the location of the keying feature 195.

FIG. 8C illustrates a cross-sectional view of an exemplary medical instrument 400 that includes the optical fiber shape sensor 140, the keying feature 195 and a reference sensor (e.g., the position sensor 150 as shown in FIG. 2) according to one embodiment of the present disclosure. The medical instrument 400 is substantially similar to the medical instrument 173 shown in FIG. 5 except for the differences described herein. In the medical instrument 400, the keying feature 195 may act to limit or eliminate the twisting or rotational displacement of the optical fiber shape sensor 140 by securing the placement of the sensor 140 within a fiber lumen 405 having an oblong or otherwise elongated cross-sectional shape similar to the cross-sectional shape of the keying feature 195. As shown in FIG. 8C, the keying feature 195 limits the rotational displacement or twist of the optical fiber shape sensor 140 relative to the medical instrument 400 generally and/or relative to the position sensor 150 specifically. Other embodiments may lack the position sensor 150. As shown in FIG. 8C, the fiber lumen 405 may be disposed within a body wall 410 of the medical instrument 400, thereby providing a conduit for the optical fiber shape sensor 140 that minimizes twist without increasing an overall outer diameter D1 of the medical instrument 400.

As shown in the embodiment of FIGS. 8A-8C, the spline 200 optionally includes a concave, curved outer mating surface 215 that is shaped and configured to mate (e.g., seat flushly) against the outer surface 210 of the optical fiber shape sensor 140. The spline sheath 205 is shaped and configured to tightly encase the optical fiber shape sensor 140 and the spline 200 and maintain their mated configuration. As shown best in FIG. 8B, bonding material 220 optionally may be included within the remaining space (i.e., space unoccupied by either the optical fiber shape sensor 140 or the spline 200) inside the spline sheath 205. The bonding material may be formed of any of a variety of materials, including, without limitation, adhesive and non-adhesive filler material.

As shown in the pictured embodiment of FIG. 8A, the spline 200 includes a length L2 that is generally at least as long as a length of the position sensor 150 (e.g., a length L3 shown in FIG. 11A). In some embodiments, the length L2 of the keying feature 195 is slightly longer than the length L3 of the position sensor 150 to account for the expected translation of the keying feature 195 (e.g., the spline 200) within the fiber lumen 405 of the instrument 400. In a given embodiment, the length L1 of the keying feature 195 may be as long as a desired length of fixed rotation of the optical fiber shape sensor 140.

In various embodiments, the keying feature 195 may be shaped and sized in any of a variety of shapes and sizes suitable for restricting rotation and twist of the optical fiber shape sensor 140. For example, although the keying feature 195 shown in FIGS. 8A and 8B is shaped as a parallel cylinder, the keying feature 195 may comprise any of a variety of shapes or structural features such as, by way of non-limiting example, a wire, a lever arm, a notch, or protrusion that is shaped and configured to interface with an inner surface or corresponding structural attribute of the medical instrument 120 (e.g., within a fiber lumen 405) to form a key-like arrangement that limits or prevents twisting or rotational movement of the optical fiber shape sensor 140 within the medical instrument 400.

In one embodiment, as shown in FIG. 9A, a keying feature 195' comprises a series of individual splines 250. In various embodiments, the keying feature 195' may comprise any of a number of individual splines of any shape and size. In the pictured embodiment, the keying feature 195' comprises four splines 250a, 250b, 250c, and 250d of similar shape and size. The splines 250a, 250b, 250c, and 250d are each attached to the optical fiber shape sensor 140 in series, with a small space in between each spline. This configuration of multiple splines coupled to the optical fiber shape sensor 140 in series may allow the sensor 140 to bend and maintain a low bending stiffness while preserving a long keyed section of the sensor 140 to prevent twisting of the sensor.

FIG. 9B illustrates a keying feature 195" comprising a series of individual splines 260a, 260b, 260c, and 260d. The keying feature 195" is substantially similar to the keying feature 195' shown in FIG. 9A except for the differences described herein. The splines 260a, 260b, 260c, and 260d are offset from each other such that adjacent splines are oriented at a slightly different angle with respect to the each other (at a slightly different radial angle with respect to the longitudinal axis OA of the optical fiber shape sensor 140). For example, in the pictured embodiment, the splines 260a and 260c are oriented at an angle α to the splines 260b and 260d. In some embodiments, the offset may be enabled by an elastomeric fastening that couples the individual splines together. The elastomeric fastening may comprise any of a variety of fastening materials, such as, by way of non-limiting example, an adhesive. The offset configuration may act as an anti-backlash mechanism that creates pre-load against a fiber lumen of the medical instrument configured to carry the optical fiber shape sensor 140 and keying feature 195" (e.g., the fiber lumen 405 shown in FIG. 8C). For example, the offset splines 260b and 260d may be biased to apply a greater degree of friction and pressure against the luminal surfaces of the fiber lumen (e.g., the fiber lumen 405 shown in FIG. 8C).

Figure 10:
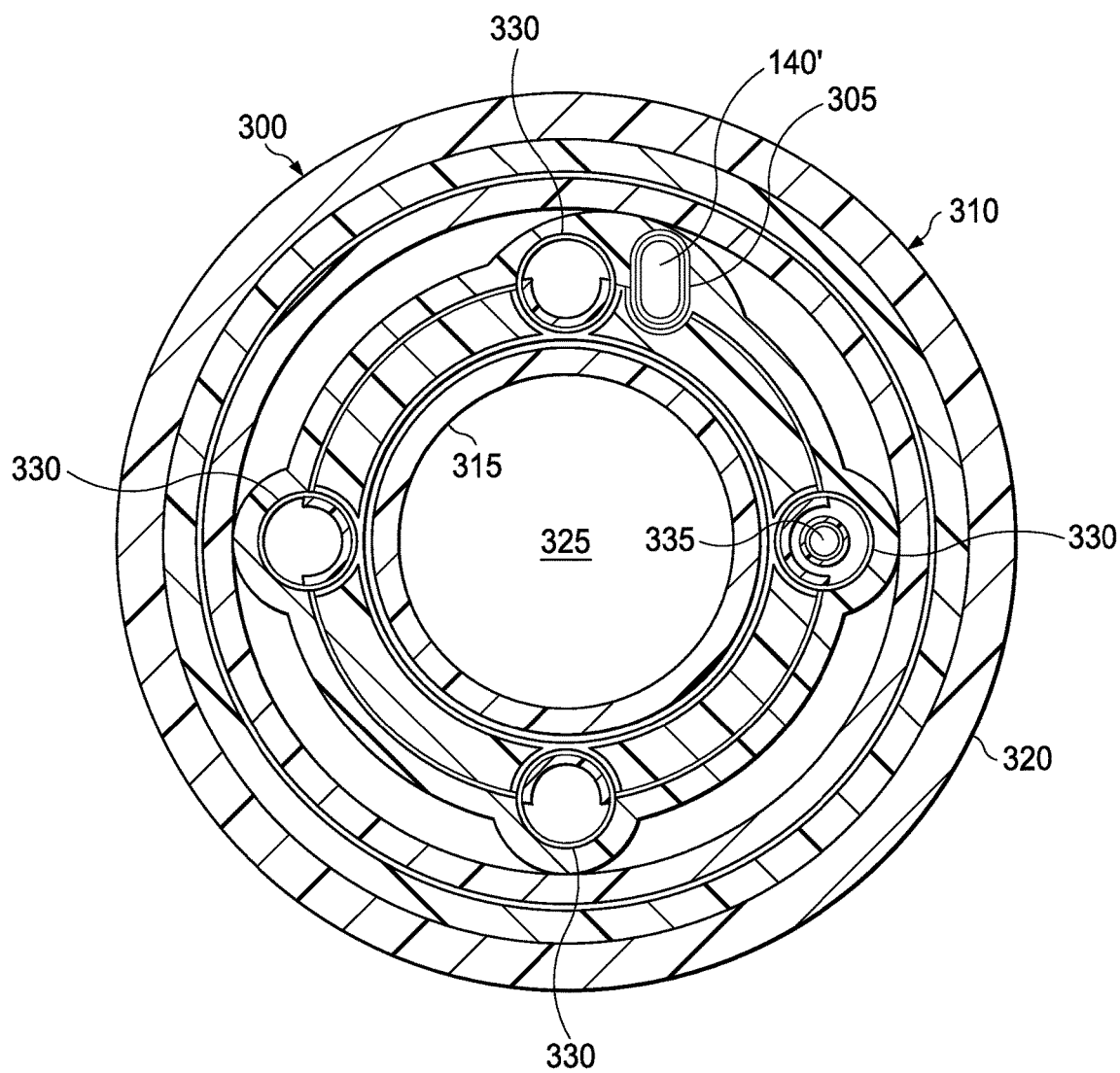
FIG. 10 is a cross-sectional view of an exemplary medical instrument including an optical fiber shape sensor and an exemplary fiber lumen according to an embodiment of the present disclosure.

FIG. 10 illustrates a cross-sectional view of an exemplary medical instrument 300 that includes a fiber lumen 305 according to one embodiment of the present disclosure. The medical instrument 300 may be the same as the medical instrument 120 described above with reference to FIG. 2. The body 310 forms an elongate, flexible tube having an inner surface 315 and an outer surface 320. The inner surface 315 of the body 310 defines a central lumen 325. The central lumen 325 may comprise the working channel of the medical instrument 300. The medical instrument 300 includes a plurality of actuation channels 330 within the body 310 that are configured to receive actuation cables 335. In other embodiments, the optical fiber shape sensor 140 can be coupled, bonded or attached to the inner surface 315 or to the outer surface 320 as appropriate. The inner surface 315 may also define a groove in which the optical fiber shape sensor 140 may be positioned. In yet other embodiments, the optical fiber shape sensor 140 can be coupled to or integral with the outer surface 320 using, for example, a suitable adhesive or bonding agent, and/or the optical fiber shape sensor 140 may be positioned within an aperture or groove that is formed within the outer surface 320. Further, the optical fiber 140 can be coupled to the instrument 300 in such a manner that a portion of the optical fiber 140 is coupled at a known reference location on the proximal portion of the instrument 300.

In the pictured embodiment, the fiber lumen 305 comprises a hollow, tubular space formed within the body 310 of the instrument 300 that is configured to receive an optical fiber shape sensor 140. In the pictured embodiment, the fiber lumen has an oblong cross-sectional shape. In other embodiments, the fiber lumen 305 may have any of a variety of cross-sectional shapes, including without limitation, ovoid, circular, rectangular, rhomboid, crescent, serpentine, and spiral. In some embodiments, as described above, the fiber lumen 305 may include at least one notch, indentation, or protrusion configured to mate with a corresponding notch, indentation, or protrusion formed along the optical fiber shape sensor 140 and/or the twist resistant feature 170. In some embodiments, the twist resistant feature 170 and the fiber lumen 305 may share a similar cross-sectional shape or profile to limit the twisting or rotational displacement of the optical fiber shape sensor 140 about the longitudinal axis OA of the optical fiber shape sensor 140 (as described above with respect to FIG. 8C).

Some embodiments may lack a separate twist resistant feature 170 or keying feature 195, and an optical fiber shape sensor 140' may be shaped to have a corresponding cross-sectional shape as the fiber lumen 305. In other words, the cross-sectional shape of the fiber lumen 305 may substantially match the cross-sectional shape of the optical fiber shape sensor 140' such that the shape of fiber lumen itself limits the twisting and rotational displacement of the optical fiber shape sensor 140'. In the pictured embodiment, the cross-sectional profile of the fiber lumen 305 is an oblong and the fiber lumen 305 snugly and slidably receives the optical fiber shape sensor 140', which has an oblong cross-sectional shape as well. In such embodiments, the twist resistant feature 170 comprises the corresponding cross-sectional shapes of the optical fiber shape sensor 140' and the fiber lumen 305.

FIGS. 11A-11D are cross-sectional views of various medical instruments that each include the optical fiber shape sensor 140 and another sensor (e.g., the position sensor 150) according to various embodiments of the present disclosure. FIGS. 11A-11D illustrate exemplary medical instruments 500, 600, 700, and 800, respectively. The medical instruments 500, 600, 700, and 800 may each be the same as the medical instrument 120 shown in FIG. 2. In some embodiments, the medical instruments 500, 600, 700, and 800 may each be substantially similar to either the medical instrument 173, 300, or 400 described above. Each of the following figures demonstrate an exemplary arrangement of the optical fiber shape sensor 140, the twist resistant feature 170 (e.g., the twist resistant feature 170', the twist resistant feature 170", and/or the keying feature 195 described above), and a reference sensor (e.g., the position sensor 150) relative to each other and relative to a distal portion of the medical instrument according to various embodiments of the present disclosure. In some embodiments, the distal portion of the medical instrument is proximal to an actively steerable section. In other embodiments, the distal portion of the medical instrument comprises a distal end of the medical instrument. In each of the illustrated embodiments, the optical fiber shape sensor 140 is fixed to either the position sensor 150 or the medical instrument at a first position along its length (e.g., fixed to create a standard reference relationship between the optical fiber shape sensor 140 and the position sensor 150), and is coupled to a twist resistant feature 170 at a second position along its length. This configuration allows for registration of the optical fiber shape sensor 140 to at least one reference point and restricting the twisting of the optical fiber shape sensor 140 while enabling it to axially translate within the medical instrument.

In some embodiments, as shown in FIG. 11A, the optical fiber shape sensor 140 is affixed to a body 505 of the medical instrument 500 at the same axial location as the position sensor 150 of the medical instrument 500 (e.g., at the same axial distance from a distal end of the medical instrument 500 along the longitudinal axis LA of the medical instrument 500) to create at least one fixed reference point for the optical fiber shape sensor 140. In the pictured embodiment, the optical fiber shape sensor 140 (within a fiber lumen 510) is coupled to the body 505 via a bonding agent 515 such as, by way of non-limiting example, an adhesive. The optical fiber shape sensor 140 is coupled to the twist resistant feature 170 near or adjacent a distal portion 520 of the medical instrument 500. Thus, the optical fiber shape sensor 140 is mechanically prevented or limited from twisting at the distal portion 520 while still being allowed to translate within the fiber lumen 510 at the distal portion 520.

In some embodiments, as shown in FIG. 11B, the optical fiber shape sensor 140 is mechanically prevented or limited from twisting at the axial location of the position sensor 150 by being coupled to the twist resistant feature 170 at the axial location of the position sensor 150. In the pictured embodiment, the optical fiber shape sensor 140 (within a fiber lumen 602) is affixed to a body 605 of the medical instrument 600 at near or adjacent a distal portion 610 of the medical instrument 600. In the pictured embodiment, the optical fiber shape sensor 140 is coupled to the body 605 via a bonding agent 615.

In some embodiments, as shown in FIG. 11C, the optical fiber shape sensor 140 is affixed to the position sensor 150, which is affixed itself to a body 705 of the medical instrument 700, to provide a reference point for the shape sensor 140. In the pictured embodiment, the position sensor 150 and the optical fiber shape sensor 140 is affixed to the body 705 via a bonding agent 710a, and the optical fiber shape sensor 140 is directly affixed to the position sensor 150, via a bonding agent 710b. The optical fiber shape sensor 140 is mechanically restrained by the twist resistant feature 170 from twisting at a distal portion 715 of the medical instrument 700 (e.g., proximal to the steerable tip). The twist resistant feature 170 is coupled to the optical fiber shape sensor 140 at the distal portion 715.

In some embodiments, as shown in FIG. 11D, the optical fiber shape sensor 140 is affixed to the position sensor 150 via a bonding agent 805. The twist resistant feature 170 is coupled to the optical fiber shape sensor 140 at the same axial position as the position sensor 150. However, both the optical fiber shape sensor 140 and the position sensor 150 are permitted to translate along the longitudinal axis LA of the medical instrument 800 (e.g., neither the optical fiber shape sensor 140 nor the position sensor 150 is affixed to an axial position within the body 810 of the medical instrument).

In some embodiments, knowledge about the axial forces causing compression and tension in the optical fiber shape sensor 140 may be used to identify the magnitude and/or effects of the twist forces and rotational displacement on the bending measurements and may also be used to separate the measurement error caused by axial forces versus twist. Information about effects of the axial forces and the extent of twist may then be used to create a mathematical model to algorithmically describe the twist between the fixed point of the optical fiber shape sensor 140 and the reference sensor (i.e., the position sensor 150) to compensate the computed bending measurements for the instrument. Knowledge of the twist measurement error within the instrument may also allow for the separation of the effects of twist and axial forces and for the identification of their respective effects on bending measurements. Algorithmic compensation techniques are then used to remove the effects of twist from the final bending measurements.

Figure 12A:
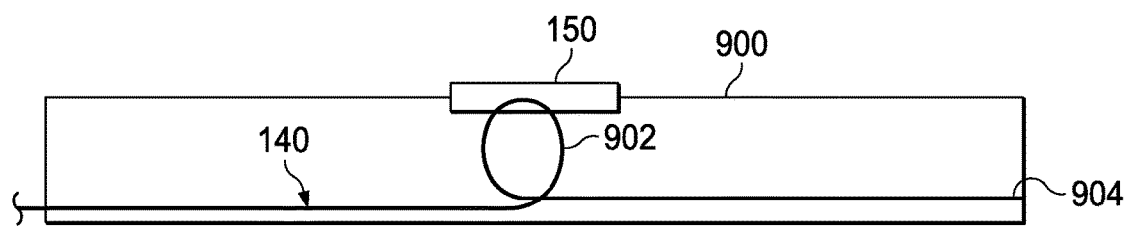
FIGS. 12A and 12B are cross-sectional views of different exemplary medical instruments that each include an optical fiber shape sensor and a twist resistant feature according to various embodiments of the present disclosure.
Figure 12B:
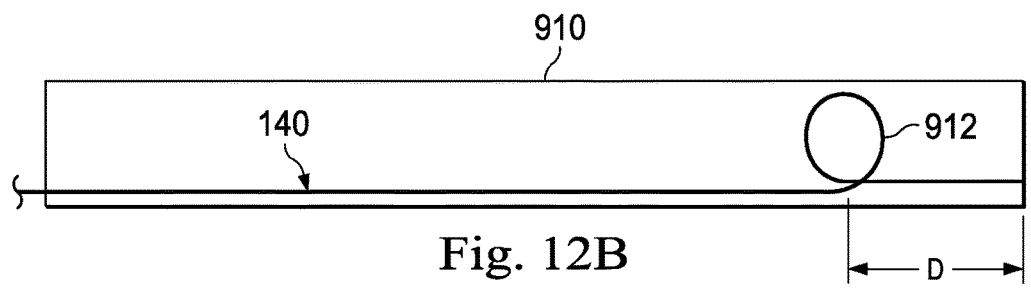

Twisting of the optical fiber can also be mitigated by reducing the overall sensed length of the shape sensor 140. FIGS. 12A and 12B illustrate medical instrument 900, 910 which mitigate twist in the sensed portion of the optical fiber shape sensor 140 by reducing the sensed portion to a length between the distal end of the instrument and a known reference point. The medical instruments 900, 910 may each be the same as the medical instrument 120 shown in FIG. 2. FIG. 12A illustrates medical instrument 900 with a fiducial marker 902 of the optical fiber shape sensor 140 coupled to the position sensor 150. The fiducial marker 902 may be a bend, loop, or other marker detectable by the tracking system 136. The fiducial marker 902 coupled to the position sensor 150 provides an axial reference point. The shape of the optical fiber 140 may be measured from the fiducial marker 902 to the distal tip 904 of the optical fiber. In this embodiment, the distal tip of the optical fiber is located at the distal tip of the medical instrument 900, but in alternative embodiments, the optical fiber may terminate proximally of the distal tip of the instrument. Fixing the location of the fiducial marker 902 in a measurable position may eliminate the need to measure the shape of the twist-prone length of optical fiber 140 between the fiducial marker 902 and the proximal end of the fiber 140.

FIG. 12B illustrates medical instrument 910 with a fiducial marker 912 of the optical fiber shape sensor 140 maintained at a fixed axial offset distance D from a distal tip of the instrument 910. The length D of the shape sensor 140 passes within a fiber lumen of the instrument 910 without constraint. The free movement of the fiber within the fiber lumen may reduce twisting in the length D of the fiber.

Figure 13:
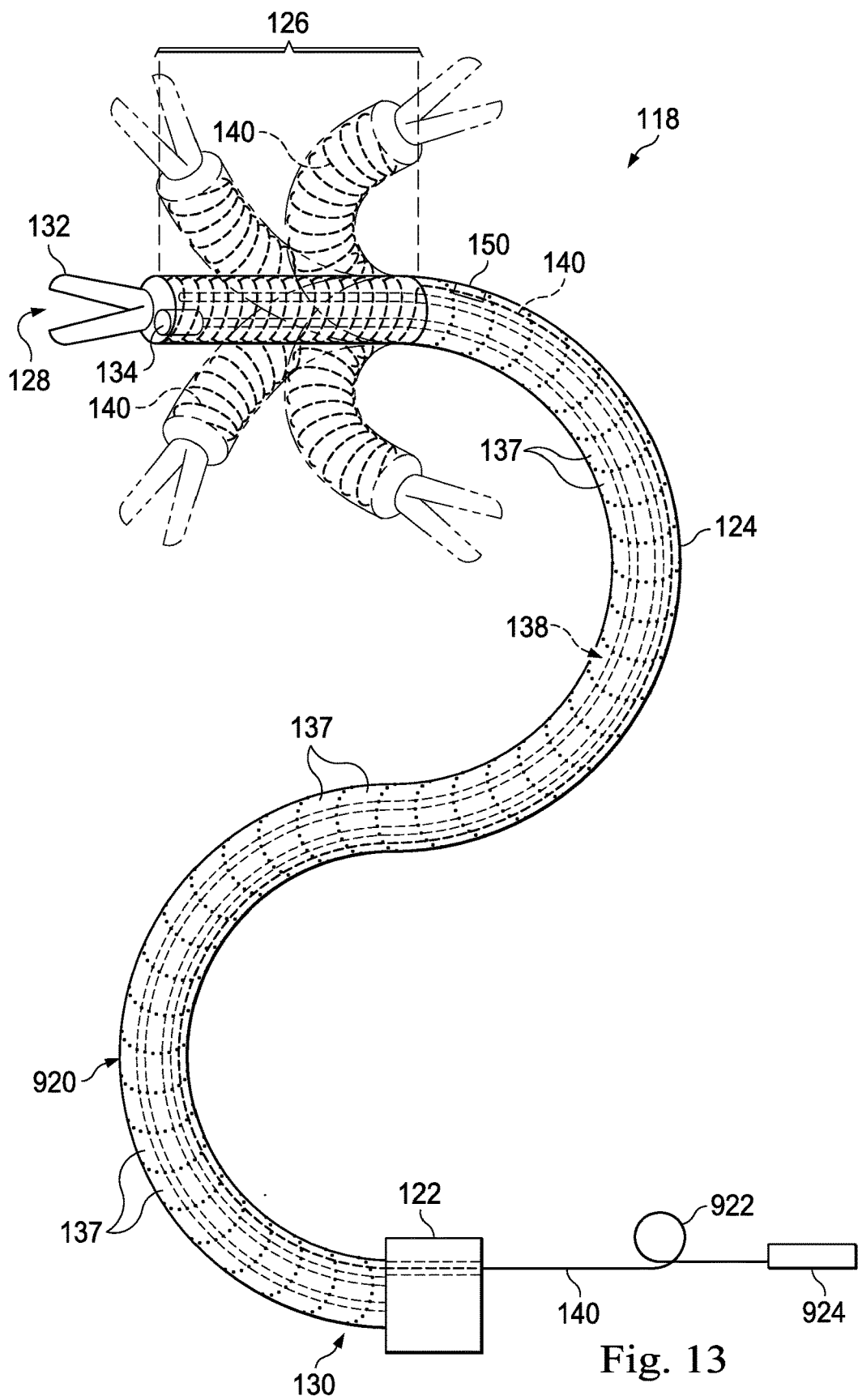
FIG. 13 illustrates a medical instrument system with a helically wrapped optical fiber shape sensor according to one embodiment of the present disclosure.

FIG. 13 illustrates medical instrument 920 which mitigates twist and/or improves the measurement for a length of the instrument by helically wrapping the optical fiber shape sensor 140 around the longitudinal axis of a distal portion of the instrument such as the steerable tip 126. The medical instrument 920 may be the same as the medical instrument 120 shown in FIG. 2. The position sensor 150 is shown located near the proximal end of the distal section 126 but may be located at other positions along the catheter. Optionally, the position sensor may be omitted. As shown in FIG. 13, the optical fiber shape sensor 140 may be helically wrapped and fixed within the wall of the flexible body 124 in the steerable tip 126. Characteristics of the helical wrap, including the angle of the wrap with respect to the longitudinal axis of the flexible body and the minimum permitted radius of bend, are selected to minimize the axial strain (compression or elongation) on the optical fiber. For example, the helical pattern characteristics may be selected to limit axial strain to less than about 1%. In this embodiment, the axial movement of the fiber 140 at the proximal end 130 of the instrument may be unconstrained. The fiber may move in and out of the proximal end 130 of the instrument, experiencing minimal axial strain near the proximal end of the instrument. The optical fiber 140 may, optionally, include a service loop 922 proximal of the instrument proximal end 130 that allows the optical fiber to move axially into and out of the instrument proximal end as needed to accommodate the movement of the instrument without straining the optical fiber. The service loop may be any slack portion of optical fiber and need not be a full loop. Optionally, a mechanical reference 924, such as a marker or sensor, may be attached to the optical fiber 140 proximal of the instrument proximal end 130. Tracking the mechanical reference provides data used to determine the twist in the proximal section of the fiber. Axial strain in an optical fiber shape sensor obscures twist measurements, but because optical fiber axial strain is minimized in the steerable section 126 of the instrument, the optical fiber 140 is able to measure twist of the distal section 126 of the instrument 920. This twist measurement may be combined with the twist measured at the proximal end of the instrument to calculate the total twist in the instrument 920.

In an alternative embodiment, the optical fiber may be helically wrapped and embedded in the wall along the entire length of the flexible body 124. With the fiber wrapped along the entire length, axial strain is minimized thus allowing twist to be measured over the length of the instrument. In this embodiment, twist may be measured without fixing the proximal end of the optical fiber to a mechanical reference.

Figure 14:
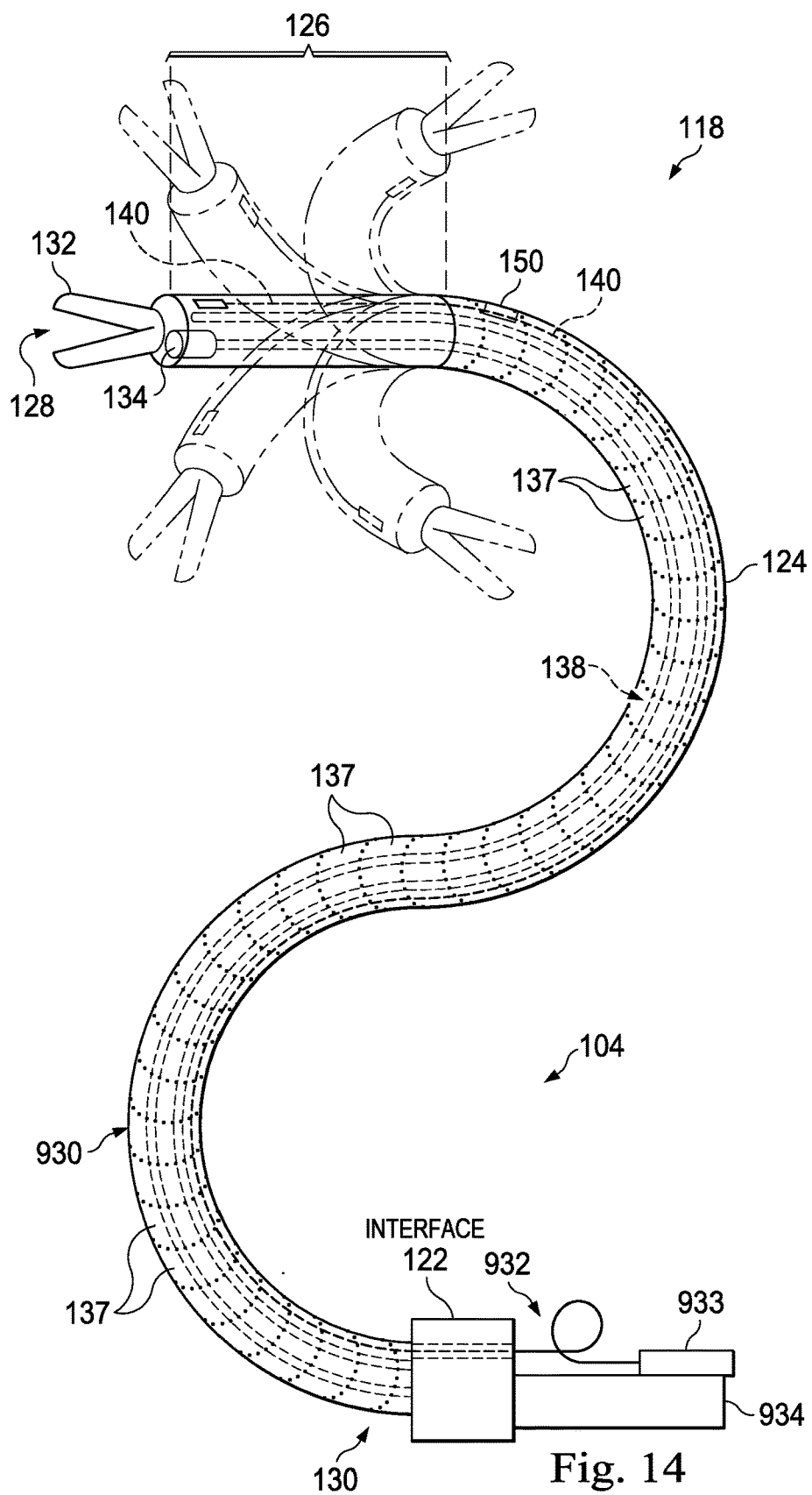
FIG. 14 illustrates a medical instrument system with a distally fixed optical fiber shape sensor according to one embodiment of the present disclosure.

FIG. 14 illustrates medical instrument 930 which mitigates twist and/or improves the measurement for any twist by fixing the distal end of the optical fiber shape sensor 140 to the distal end of flexible body 124 and fixing the proximal end of the optical fiber shape sensor in a known or measurable position. The medical instrument 930 may be the same as the medical instrument 120 shown in FIG. 2. The position sensor 150 is shown located near the proximal end of the distal section 126 but may be located at other positions along the catheter. Optionally, the position sensor may be omitted. The optical fiber may be attached to the distal end of the flexible body, for example, using an adhesive, a mechanical coupling, or by embedding the fiber in the wall of the flexible body. In this embodiment, the portion of the fiber 140, within the flexible body 124 and proximal of the distal fixation location, may float freely within a shape sensor lumen of the flexible body. The optical fiber 140 may include a service loop 932 proximal of the instrument proximal end 130 that allows the optical fiber to move axially into and out of the instrument proximal end as needed when the instrument is bent. Because the fiber is allowed to move in and out of the proximal end 130 of the instrument, it may experience minimal axial strain as the instrument bends. The proximal end of the optical fiber 140 may be coupled to a fixture 933 fixed in a known position with reference to a known coordinate system. The coordinate system may be the fixed with respect to a teleoperational arm 934 that holds the instrument. The teleoperational arm 934 may be referenced to a patient image, such as a preoperative CT image, or to a position sensor attached to the patient that references to the coordinate system of the teleoperation arm 934. In this embodiment, the twist of the catheter is measured with the optical fiber shape sensor 140 from the fixture 933 to the distal fixation point of the fiber.

In some configurations, it may be desirable to infer twist at a particular location using a mathematical or empirical model of twist along the length of the fiber. In one such embodiment, the fiber may be affixed at two ends with an appropriate amount of slack to allow sliding along the fiber axis (e.g. FIG. 14). The twist may be calculated at a reference frame along the catheter (for example at the EM sensor 150). Though twist can be measured directly by the fiber, a mathematical model may be helpful in measuring the twist of the fiber relative to the lumen or catheter should the fiber be able to twist freely relative to a desired frame of reference on the catheter. One model assumes that the twist of the fiber relative to the lumen scales linearly with distance from a fixed point (e.g. the catheter tip). Other mathematical models might include a polynomial or exponential fit to the relative twist. Alternatively, twist might be measured empirically by some other means to measure twist of the fiber relative to the catheter for specific bend angles or directions.

If using two or multiple shape sensors at known locations within the catheter, measurement of catheter twist may be measured using the relative shape (position) of the fibers irrespective of twist profile of any individual shape sensor. In this configuration, fibers could be allowed to float freely in a lumen to allow mitigation of any imposed twist. Following the measurement of twist, a reference frame on the catheter such as the EM sensor could be measured at some point relative to multiple sensors.

Although the optical fiber shape sensors and positional sensor systems have been described herein with respect to teleoperated or hand operated surgical systems, these sensors can find application in a variety of medical and non-medical instruments in which accurate instrument bending measurements would otherwise be compromised by twist or other rotational displacements of the shape sensors.

One or more elements in embodiments of the invention may be implemented in software to execute on a processor of a computer system such as control system 108. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus comprising:
   an instrument including an elongated shaft;
   a first shape sensor including an elongated optical fiber extending within the elongated shaft at a first radial distance from a neutral axis; and
   a twist resistant feature configured to reduce twisting of the elongated optical fiber relative to the elongated shaft while permitting axial translation of the elongated optical fiber within the elongated shaft, wherein the twist resistant feature includes a keying feature that includes:
   a first spline disposed along the first shape sensor; and
   a second spline disposed along the first shape sensor and separated from the first spline by a region of the first shape sensor that is free of the twist resistant feature.

2. The apparatus of claim 1, further comprising a tracking system adapted to receive shape data from the first shape sensor for calculating a bend measurement for the instrument.

3. The apparatus of claim 1, wherein the twist resistant feature is coupled to the elongated shaft.

4. The apparatus of claim 1, wherein the twist resistant feature is coupled to at least a portion of the elongated optical fiber.

5. The apparatus of claim 1, wherein the keying feature further includes a fiber lumen extending within the elongated shaft and having a cross-sectional shape that is configured to complement the first spline and the second spline, wherein the fiber lumen interfaces with the first spline and the second spline to limit the twisting of the elongated optical fiber within the fiber lumen.

6. The apparatus of claim 5, wherein the cross-sectional shape of the fiber lumen is oblong.

7. The apparatus of claim 1, wherein the keying feature comprises a first spline sheath configured to encase the first spline and at least a portion of the elongated optical fiber to maintain their mated configuration and a second spline sheath configured to encase the second spline and at least a portion of the elongated optical fiber to maintain their mated configuration.

8. The apparatus of claim 1, wherein the first spline is coupled to the elongated optical fiber at a first radial angle and the second spline is coupled to the elongated optical fiber at a second radial angle that is offset from the first radial angle.

9. The apparatus of claim 1, further comprising an elastomeric fastening coupling the first spline and the second spline and configured to maintain first spline and the second spline in an offset configuration.

10. The apparatus of claim 9, wherein the keying feature further includes a fiber lumen extending within the elongated shaft to receive the first shape sensor, and wherein the offset configuration of the first spline and the second spline is configured to apply pressure against the fiber lumen.

11. The apparatus of claim 10, wherein the offset configuration is configured to increase friction between the fiber lumen and the first and second splines.

12. The apparatus of claim 10, wherein the offset configuration is configured to create a pre-load against the fiber lumen.

13. The apparatus of claim 1, further comprising a position sensor disposed within the elongated shaft at a first axial distance from a distal portion of the elongated shaft.

14. The apparatus of claim 13, wherein the elongated optical fiber is affixed to the elongated shaft at the first axial distance and the twist resistant feature is coupled to the elongated optical fiber adjacent the distal portion of the elongated shaft.

15. The apparatus of claim 13, wherein the twist resistant feature is coupled to the elongated optical fiber at the first axial distance and the elongated optical fiber is affixed to the elongated shaft at the distal portion of the elongated shaft.

16. The apparatus of claim 13, wherein the elongated optical fiber is affixed to the position sensor at the first axial distance, the position sensor is affixed to the elongated shaft at the first axial distance, and the twist resistant feature is coupled to the elongated optical fiber at the distal portion of the elongated shaft.

17. The apparatus of claim 13, wherein the elongated optical fiber is affixed to the position sensor at the first axial distance, the twist resistant feature is coupled to the elongated optical fiber at the first axial distance, and the elongated optical fiber and the position sensor are able to axially translate along a longitudinal axis of the elongated shaft.

18. The apparatus of claim 1, wherein each of the first spline and the second spline includes a member from a group consisting of: a metal wire, a polymeric rod, and a glass fiber.

19. The apparatus of claim 1, wherein each of the first spline and the second spline includes a cylindrical portion and a biconcave prism portion disposed between the cylindrical portion and the first shape sensor.

20. The apparatus of claim 19, wherein each of the first spline and the second spline further includes:

a spline sheath disposed around the respective spline and the first shape sensor; and a bonding material disposed between the biconcave prism portion and the spline sheath.

21. The apparatus of claim 1, further comprising a position sensor disposed within the elongated shaft, wherein a length of the keying feature is longer than a length of the position sensor.

22. The apparatus of claim 1, wherein the first spline and the second spline are coupled only by the first shape sensor.

23. The apparatus of claim 1, wherein an outermost portion of the first spline disposed away from the first shape sensor is uncoupled from an outermost portion of the second spline disposed away from the first shape sensor.

* * * * *